US011176697B2

(12) United States Patent
Traverso et al.

(10) Patent No.: US 11,176,697 B2
(45) Date of Patent: Nov. 16, 2021

(54) METHOD FOR CONTROLLING IMAGE APPEARANCE FEATURES IN MRI SYSTEMS, IMAGE APPEARANCE FEATURE CONTROL USER INTERFACE OPERATING ACCORDING TO THE SAID METHOD AND MRI SYSTEM COMPRISING SAID USER INTERFACE

(71) Applicant: Esaote S.p.A., Genoa (IT)

(72) Inventors: Paolo Traverso, Genoa (IT); Erminio Bassi, Genoa (IT)

(73) Assignee: ESAOTE S.P.A., Genoa (IT)

( * ) Notice: Subject to any disclaimer, the term of this patent is extended or adjusted under 35 U.S.C. 154(b) by 385 days.

(21) Appl. No.: 15/911,381

(22) Filed: Mar. 5, 2018

(65) Prior Publication Data

US 2018/0260971 A1    Sep. 13, 2018

(30) Foreign Application Priority Data

Mar. 8, 2017  (EP) ..................... 17159863

(51) Int. Cl.
*G06T 7/70* (2017.01)
*A61B 5/055* (2006.01)
(Continued)

(52) U.S. Cl.
CPC ............... *G06T 7/70* (2017.01); *A61B 5/055* (2013.01); *G01R 33/543* (2013.01);
(Continued)

(58) Field of Classification Search
CPC .............. G06T 7/174; G06T 7/0014; G06T 2207/10088; G06T 2207/30004;
(Continued)

(56) References Cited

U.S. PATENT DOCUMENTS 6,603,494 B1 * 8/2003 Banks ................... A61B 5/055
715/807
2002/0011844 A1 * 1/2002 Biglieri ............ G01R 33/34046
324/318
(Continued)

OTHER PUBLICATIONS

Young ["Automated planning of MRI neuro scans", Proceedings of SPIE—The International Society for Optical Engineering • Mar. 2006] (Year: 2006).*

*Primary Examiner* — Oommen Jacob
(74) *Attorney, Agent, or Firm* — Buchanan Ingersoll & Rooney PC

(57) ABSTRACT

Method for controlling image appearance features in MRI systems, image appearance feature control user interface operating according to the method and MRI system including the user interface. There is provided an automatic scan planning module including a memory in which a look up table or a database of examination kind specific settings of the MRI system is stored univocally associating a specific kind of examination with a factory pre-defined experimentally and empirically determined optimum combination of settings of the MRI system, the automatic scan planning module controlling a user interface displaying a list of alternative specific kinds of examinations and providing a selection organ for the user, for selecting one of the specific kinds of examinations. Upon input of the selection of the kind of examination, the automatic scan planning module configures the MRI system automatically with the image acquisition settings corresponding to the selected specific kind of examination.

18 Claims, 20 Drawing Sheets

(51) Int. Cl.
*G06T 7/00* (2017.01)
*G06T 7/11* (2017.01)
*G01R 33/56* (2006.01)
*G06T 7/174* (2017.01)
*G01R 33/54* (2006.01)
*G01R 33/483* (2006.01)

(52) U.S. Cl.
CPC ........ *G01R 33/5608* (2013.01); *G06T 7/0014* (2013.01); *G06T 7/11* (2017.01); *G06T 7/174* (2017.01); *G01R 33/4835* (2013.01); *G06T 2207/10088* (2013.01); *G06T 2207/30004* (2013.01)

(58) Field of Classification Search
CPC .. G06T 7/70; G06T 7/11; A61B 5/055; A61B 5/00; A61B 5/7435; A61B 6/563; A61B 6/566; A61B 8/56; A61B 8/565; A61B 6/581; A61B 5/411; A61B 6/00; A61B 8/00; A61B 6/467; A61B 6/465; A61B 6/469; A61B 6/468; G01R 33/543; G01R 33/5608; G01R 33/4835; A61N 5/103; G16H 40/63; G06F 3/0481; G06F 19/321; G06F 19/324; G06F 19/3418; G06F 19/00; G06Q 50/24

See application file for complete search history.

(56) References Cited

U.S. PATENT DOCUMENTS

| | | | |
|---|---|---|---|
| 2004/0267122 A1* | 12/2004 | Nadadur | A61B 8/465 600/440 |
| 2006/0079778 A1* | 4/2006 | Mo | G01S 7/52026 600/447 |
| 2007/0053503 A1* | 3/2007 | Zelnik | A61B 6/04 378/205 |
| 2007/0078306 A1* | 4/2007 | Allison | A61N 5/103 600/300 |
| 2009/0214094 A1* | 8/2009 | Williams | A61B 6/481 382/131 |
| 2009/0237077 A1* | 9/2009 | Vaughan | G01R 33/3664 324/307 |
| 2011/0148411 A1* | 6/2011 | Bottomley | G01R 33/58 324/309 |
| 2018/0260971 A1* | 9/2018 | Traverso | G06T 7/70 |

* cited by examiner

- Three Orthonormal Anatomical Planes are defined: Transverse, Sagittal, and Coronal
- Intersection of the transverse and sagittal plane defines the anterior-posterior (AP) axis.
- The intersection of the sagittal and coronal plane defines the feet-head (FH) axis.
- The intersection of the transverse and coronal plane defines the left-right (LR) axis.

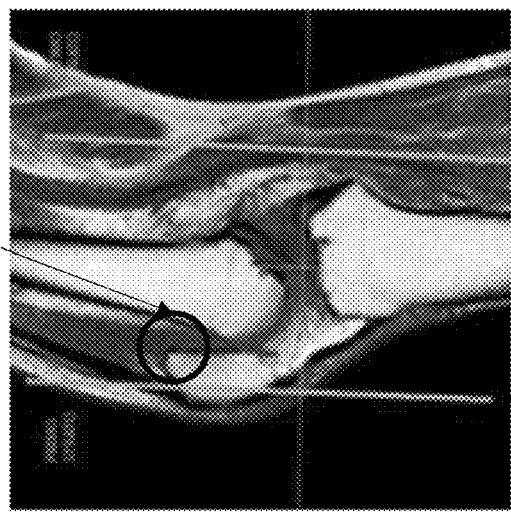
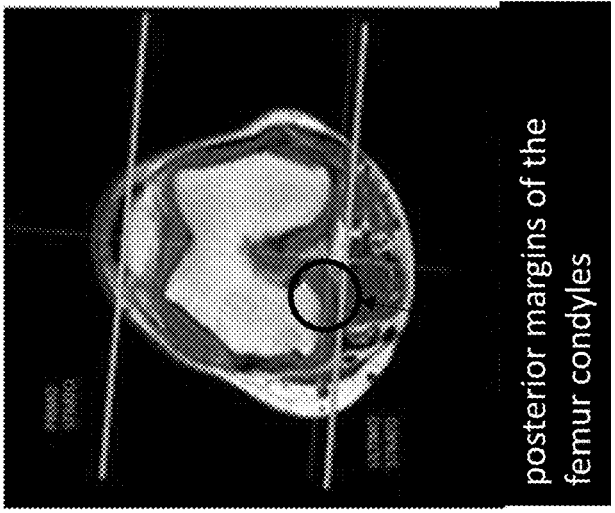
Fig.12

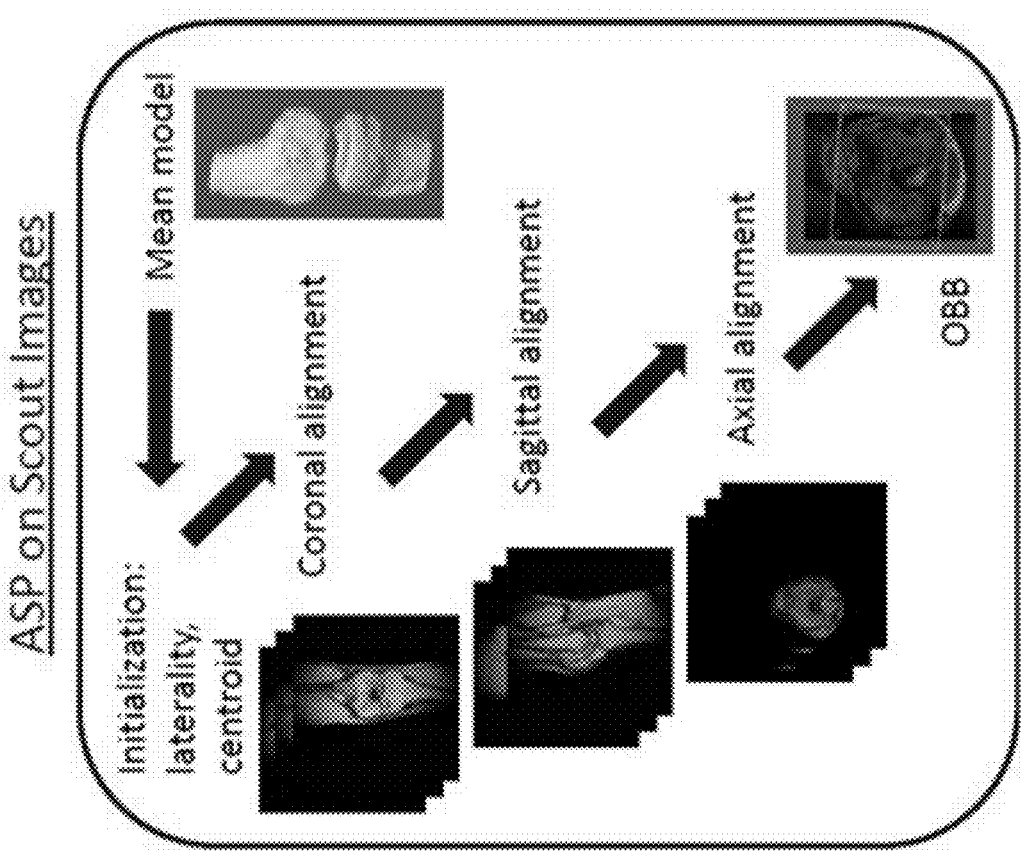

Parameter Settings:

Chamfer Matching

1620 → • Coronal scout images
 ○ Model scaling
  * 0.95, 1.0, 1.05
 ○ Model translations
  * X: ±10 mm in 5mm steps
  * Y: ±10 mm in 5mm steps
  * Z: ±5 mm in 5mm steps 1630 → • Sagittal scout images
 ○ Model translations
  * X: ±2.5 mm in 2.5mm steps
  * Y: ±2.5 mm in 2.5mm steps
  * Z: ±5 mm in 2.5mm steps 1640 → • Axial scout images
 ○ Model scaling
  * 0.95, 1.0, 1.05
 ○ Model translations
  * X: ±2.5 mm in 2.5mm steps
  * Y: ±2.5 mm in 2.5mm steps
  * Z: 0 mm
 ○ Model rotations
  * Around z-axis: ±9° in 3° steps

Fig.16

METHOD FOR CONTROLLING IMAGE APPEARANCE FEATURES IN MRI SYSTEMS, IMAGE APPEARANCE FEATURE CONTROL USER INTERFACE OPERATING ACCORDING TO THE SAID METHOD AND MRI SYSTEM COMPRISING SAID USER INTERFACE

BACKGROUND OF THE INVENTION

The disclosure relates to a method for controlling image appearance features in MRI systems by setting the values of workflow setting parameters having an influence on the final image appearance in such a way that one or more image appearance features are set in desired condition of providing the said finale image appearance.

Current user interfaces of standard MRI systems are based on controls which are not logically correlated to final image appearance. It is the operator/user who has to translate his experience/know-how in proper system's settings adapted to the real-time scan needs. The current image end user controls are based on standard workflow setting parameters which are more related to the physics of the imaging process than to the final appearance of the images visualized on the display. For doctors or paramedical operators which have a limited knowing of the system workflow and of the physical processes governing the NMR imaging it is often difficult to influence the image appearance by controlling the values of the said standard workflow setting parameters. Furthermore, many different standard workflow setting parameters have an influence on a certain image appearance feature so that the operator has to control several different setting parameters in order to modify the image appearance.

Furthermore, operators with limited skills of the system workflow may incur in reaching a "bad tuning" configuration of the setting parameters which provide for a desired image appearance but which are non-optimal or detrimental for obtaining quality images.

One example of the task to be carried out by an operator of an MRI apparatus when carrying out an imaging scan consists in acquiring a scout image, which can be a 3D scout image or a 2D scout image consisting in acquiring the image of at least three slices along three orientations which are perpendicular one to the other as typically a slice along the transversal, the coronal and the sagittal plane.

FIG. 5 defines unambiguously the transversal, coronal and sagittal planes. According to the FIG. 5 the three orthonormal anatomical planes are defined: Transverse, Sagittal, and Coronal Intersection of the transverse and sagittal plane defines the anterior-posterior (AP) axis. The intersection of the sagittal and coronal plane defines the feet-head (FH) axis and the intersection of the transverse and coronal plane defines the left-right (LR) axis.

An example of a 2D scout image comprising images along slices oriented according to the transverse, coronal and sagittal planes, respectively T, C and S is illustrated in FIG. 8.

According to the current practice, the scout images are analysed manually by a technician who decides about the Region of Interest and the Slice Position and Orientation for obtaining the more detailed diagnostic images. The technician can use the already acquired images as Reference for positioning the other Images. In order to carry out the positioning the operator has to individuate anatomical references on the scout images. This requires that the operator has skills in recognizing anatomic structures so that in order to carry out NMR imaging the operator need to be an individual having higher educational degrees and this increases the examination costs.

SUMMARY

An object of the present disclosure consists in providing an improved method for carrying out MRI imaging which simplifies the tasks of setting the proper parameters for carrying out the examination.

A further object is to provide for an improved imaging method requesting less skilled operators for servicing the MRI apparatus and setting it in order to acquire diagnostically useful images.

Still a further object consists in providing a imaging method which reduces the time needed to apply proper settings of an MRI apparatus which are related to a specific anatomic district and to a specific imaging protocol which is particularly designed for a certain diagnosis.

Still another object of the present disclosure is to provide for a system which is designed for carrying out the improved method for selecting and applying system setting parameters or protocols.

Still another object is to provide for a smart User Interface not requiring a specific skill on more technical and physical aspects of medical NMR imaging which are, di per se, out of usual background of final users.

In the present description and in the claims, if not further specified, the term "parameter" or the term "setting" or "settings" include both physical and geometrical parameters to be supplied to the MRI apparatus in order to carry out an imaging session.

According to an embodiment of the present invention, an MRI system is provided which comprises:
- a cavity for accommodating a target body under examination or a part thereof
- a magnet for generating a static magnetic field in a volume of space;
- gradient coils for generating gradient magnetic fields in addition to the static magnetic field according to three spatial directions;
- a control unit configured to drive and control the gradient coils and the magnet;
- a transmission antenna connected to an excitation signal sequence generator for transmitting spin echo excitations signals into the cavity housing the target body;
- a receipt antenna for receiving the MRI signals caused by the excitation signals;
- an MRI receipt signals processing unit and image generation unit for processing the signals and extracting image data information and for generating the images;
- a display unit for displaying the reconstructed images;
- a control unit managing the excitation signal sequence generator, the receipt signals processing unit, image generation unit and the display;
- a user interface for input of MRI image acquisition settings to be specified by the user before starting with the image acquisition session
- an automatic scan planning module comprising a memory in which a look up table or a database of examination kind specific settings of the MRI system is stored univocally associating a specific kind of examination with a factory pre-defined experimentally and empirically determined optimum combination of settings of the MRI system, the said automatic scan planning module controlling a user interface displaying a list of alternative specific kind of examinations and providing a selection organ for the user, for selecting one of the specific kind of examinations;

upon input of the selection of the kind of examination, the automatic scan planning module configures the MRI system automatically with the image acquisition settings corresponding to the selected specific kind of examination.

The processing units referred to herein may be hardware processing units.

According to an embodiment herein the automatic scan planning module comprises a database of anatomical districts corresponding to anatomical districts which are typically subjected to MRI diagnostic examination the said anatomical districts are related each one to one or more image acquisition settings and/or imaging protocols specifically suitable for a certain diagnosis.

According to still another embodiment the image acquisition settings comprise geometric parameters which are related to orientation and positioning of one or more image slices specifically suitable for imaging a certain anatomical district and for a certain diagnosis and/or physical parameters which relates to imaging settings like a specific sequence and other parameters.

Another embodiment provides for an MRI system comprising a user interface with a display and input organs, the display being configured to display a selection list of anatomic districts each anatomic district being selectable by the input organs and providing a link to a list of specific diagnosis related to the selected anatomic district, the selection of a diagnosis being automatically related to specific image acquisition settings and triggering an automatic application of the said image acquisition settings to the MRI apparatus.

According to an embodiment the MRI system comprises a user interface including input organs for modifying at least one of the automatically defined factory pre-defined experimentally and empirically determined optimum combination of settings of the MRI system corresponding to a selection of a specific anatomical district and/or kind of examination.

According to sill another embodiment the MRI system according to the present invention comprises an image processing unit configured to receive the image data of a scout image which is acquired before setting the examination kind specific settings of the MRI system, the said image processing unit executing image processing of the scout image or of a reference image received or taken from a memory, for determining the kind, the position and orientation in the image of one or more tissues, organs or anatomical details and automatically configuring lists of available alternative specific kind of examinations and providing a selection organ for the user, for selecting one of the specific kind of examinations which are filtered from a global list using as a filter the output of the object recognition process.

According to an improvement the system is provided with a processing unit configured to automatically identify the kind, the position and orientation in the scout image or reference image of one or more tissues, organs or anatomical details and to automatically select and apply the image acquisition settings suitable for the said automatically identified kind, position and orientation in the scout image of one or more tissues, organs or anatomical details.

According to still another embodiment of the MRI system, the said factory pre-defined, experimentally and empirically determined settings are at least one or a combination of at least two of the following parameters: region of interest (ROI), orientation of image slices, number of image slices and position in relation to the ROI, resolution, excitation sequence, slice thickness.

According to a further embodiment, the processing unit comprises or is connected to a memory configured to store a database of scout images or of reference images and of corresponding imaging slice orientations for each anatomic district and each specific diagnosis, the processing unit being configured to processing the scout images acquired for an imaging session for automatically identify the anatomic district and apply the position and orientation of the slice along which an image is to be acquired according to an imaging protocol which is specific for a certain diagnosis and is stored in the said database.

The present disclosure relates also to a method which method comprises the following steps:

providing a look up table or a database of examination kind specific settings of an MRI system univocally associating a specific kind of examination with a factory pre-defined experimentally and empirically determined optimum combination of settings of the MRI system, providing a user interface displaying the said list of specific kind of examinations which are selectable by the user through the said interface;

automatically configuring the MRI system with the factory pre-defined experimentally and empirically determined optimum combination of settings of the MRI system corresponding to the selected specific kind of examination in the said look up table or in the said database;

carrying out the MRI examination with the above defined configuration of the MRI-System.

According to a further embodiment the method provides for a step of:

Providing a list of anatomic districts which are typically subjected to MRI examination for the diagnosis of one or more pathologies;

Linking each anatomic district to the one or more diagnosis;

Linking each of the one or more diagnosis to one or more specific kind of examinations;

Displaying the list of the anatomic district;

Automatically displaying the list of possible diagnosis related to an anatomic district upon selection of the said anatomic district;

Automatically selecting the factory pre-defined experimentally and empirically determined optimum combination of settings of the MRI system corresponding to the selected specific kind of examination and Automatically configuring the MRI system according to the said settings of the MRI system.

According to still another embodiment when for a diagnosis there are available in the database of the kind of examination of two or more different factory pre-defined experimentally and empirically determined optimum combination of settings of the MRI system, the method provides for displaying the two or more different factory pre-defined experimentally and empirically determined optimum combination of settings of the MRI system for selection by the user and applying the factory pre-defined experimentally and empirically determined optimum combination of settings of the MRI system which has been selected by the user.

A further embodiment of the method provides that the factory pre-defined settings can be modified by the user after having selected a specific kind of diagnosis and the said modified settings may be stored as an alternative user pre-defined setting and is suggested together or in place of the originally factory pre-defined settings.

According to a further embodiment when a user modifies one or more of the pre-defined settings, the said modified setting is stored as the default pre-defined setting to be applied in a future identical case. According to an embodiment the processing unit may be configured to receive a user input consisting in modified settings and to amend the suggested pre-defined settings with the modified data of the user, by electing this modified settings as the future default pre-defined settings and by storing the said new default pre-defined settings.

According to an improvement, one embodiment is provided with a user confirmation step for allowing the system to modify the pre-defined default setting according to the modifications inputted by the user, so to avoid that a specific setting modified in view of one case occurred only once will become a general default setting.

Still according to a further embodiment of the method the factory pre-defined settings are at least one or a combination of at least two of the following parameters: region of interest (ROI), orientation of image slices, number of image slices and position in relation to the ROI, resolution, excitation sequence, slice thickness.

A further embodiment of the method provides the steps of acquiring a scout image or of taking a reference image from a reference image memory before setting the examination kind specific settings of the MRI system;
  the scout or reference image being processed by an imaging processing tool such as an object recognition tool for determining the kind, the position and orientation in the image of one or more tissues, organs or anatomical details and
  automatically configuring lists of available alternative specific kind of examinations and
  providing a selection organ for the user, for selecting one of the specific kind of examinations which are filtered from a global list using as a filter the output of the image processing tool.

According to an embodiment the method is directed to an automatic positioning and orientation of image slices for a specific anatomic district and a specific diagnosis of a pathology of the said anatomic district and which method provides the following steps:
  Selecting an anatomic district corresponding to the object to be examined;
  Selecting imaging parameters setting among preconfigured available imaging settings for the said anatomic district suitable for a diagnosis of a pathology of the said anatomic district;
  the said imaging settings comprising position and orientation information of the image slices to be acquired in relation to the diagnosis of the pathology of the anatomic district and in relation scout images of a scout image database of the said anatomic district;
  Acquiring a scout image of the object to be examined which scout image comprises at least images along three slices each slice being oriented along one orthonormal planes oriented along the transversal, coronal and sagittal direction;
  Processing the acquired scout image for identifying anatomic references common to the scout images of a scout image database of the same anatomic district of the acquired scout images of the anatomic district under examination;
  Shifting the acquired scout image relatively to the scout images of the scout image database in order to register the anatomic references on the acquired scout image of the object under examination with the corresponding anatomic references on the scout images of the scout image database of the same anatomic district and applying the position and orientation of the image slices related to the scout images in the scout image database to the acquired scout image of the object in examination.

The above combination of steps can be also applied to the case in which one or more reference images are available instead of acquiring a scout image. This images may be scout images or other images acquired in previous imaging sessions. In the case of using reference images, in the above combination of steps the acquisition along the three orthonormal planes is omitted since it is not necessary According to still a further embodiment, the step of shifting the acquired scout image or the relatively to the scout images of the scout image database or relatively to one or more reference images of a reference images database, is carried out by selection one or more limited areas on the said images and carrying out the registration only in relation to the pixels of the said one or more limited areas that has been selected.

Particularly the said limited areas of the images coincide with areas of the images containing the image of a specific anatomic marker of the object being imaged.

According to still another embodiment of the method the settings for acquiring images comprises also physical parameter settings of the MRI imaging process.

Further advantages of the present invention and further improvements are described in the following detailed description.

BRIEF DESCRIPTION OF THE DRAWINGS

FIGS. 11 to 13 illustrate the slice orientation and positioning results according to the method of the present invention each one along a transversal, coronal and sagittal positioning for a general case.

FIG. 16 illustrates a table which puts in relation the flow of the parameters settings and the corresponding effect on the images relatively to a specific automatic positioning and orienting of the slices along which acquiring the images of the object to be examined.

DETAILED DESCRIPTION OF THE EMBODIMENTS

The term centroids used in the description is to be intended as including all the geometric and/or physical features of the marked or of a selected limited area of an image.

Figure 1:
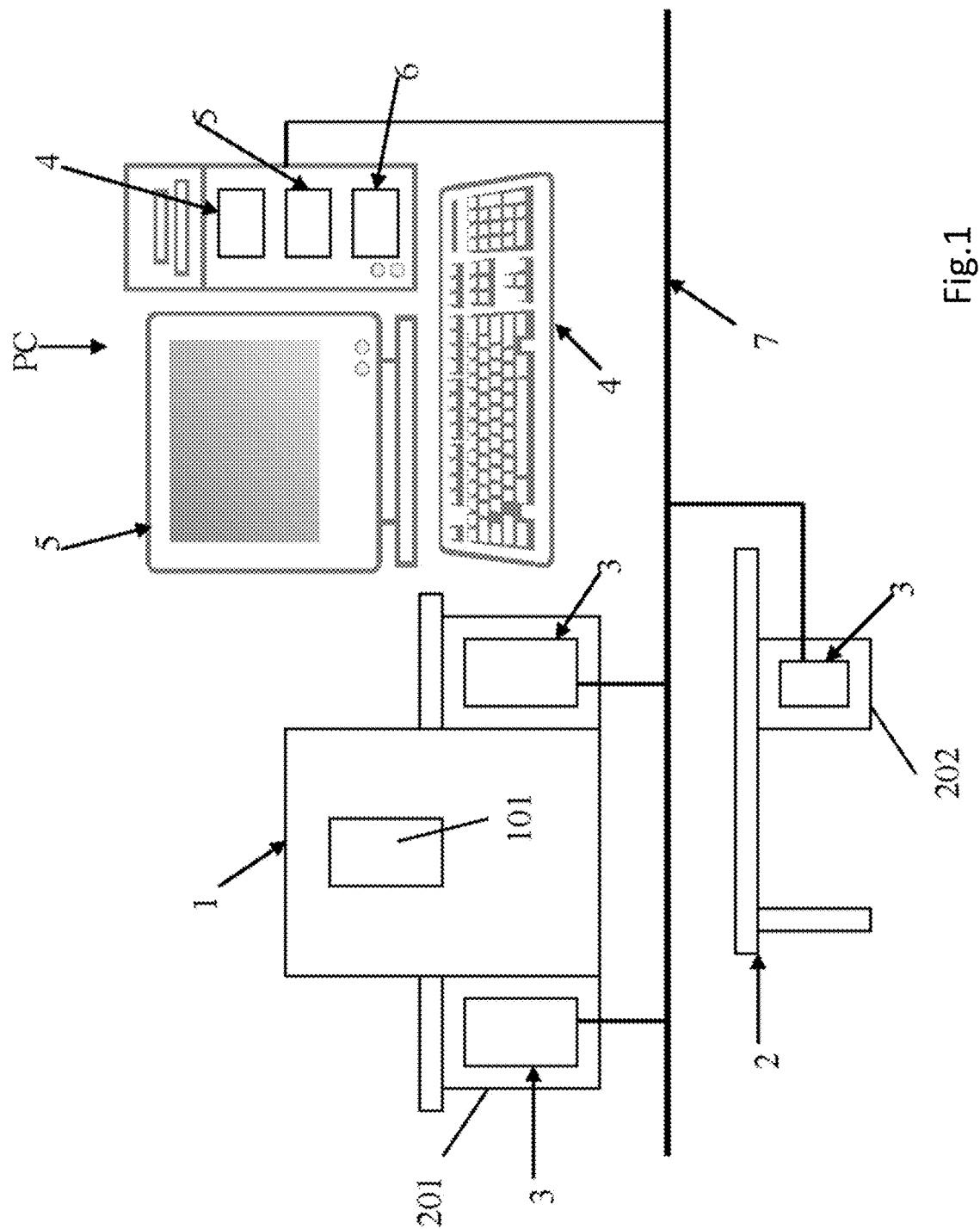
FIG. 1 is a schematic block diagram of an embodiment of an MRI system according to the present invention.

With reference to FIG. 1, an embodiment of Nuclear Magnetic Resonance imaging machine suitable to be configured for carrying out the present invention comprises a signal exciting and receiving unit consisting of a magnetic unit 1. The magnetic unit includes permanent or resistive or superconducting magnets for generating a static field inside a cavity 101 which is designed to receive the patient body or a part thereof, particularly a limited anatomic region, such as a leg, an arm, the head, etc.

As is generally known, different coils are associated to the static field generating magnet, including:

excitation coils, for exciting nuclear spins;

magnetic gradient generating coils, for selecting the section plane along which imaging has to be performed, for encoding nuclear spins to univocally identify the signals transmitted at a predetermined space position and univocally assign the received data to a predetermined pixel of a pixel matrix which forms the displayed image;

receiving coils, for receiving magnetic resonance echoes.

Also, other means are provided, such as temperature control sensors and/or means for heat increase or generation and means for heat dissipation, which are designed to set and maintain a predetermined operating temperature, etc.

All the above elements are well-known and widely used in Nuclear Magnetic Resonance imaging machines of any type and size, both for total body machines, i.e. those designed to accommodate the whole patient body or a substantial part thereof, and for dedicated machines, i.e. those adapted to only accommodate specific limbs or limited parts or regions of the patient body.

The geometry of the magnetic structure, i.e. of the cavity for accommodating the body under examination or the part thereof may also be of any type, and particularly either of the open C- or U-shaped type, or consisting of two poles separated by columns, or of the annular, closed type.

The machine shown in FIG. 1 is a non-limiting exemplary embodiment having a closed, i.e. annular magnetic structure and the cavity is only open at the two end sides transverse to the axis. C or U shaped magnets have three open sides, while other magnets are formed by only two opposite poles which limit a gantry being opened along the peripheral sides of the two poles. Also magnets comprising a limitation only on one side which is formed for example by only one pole plate, the object to be imaged being placed on one side of the said pole plate which is completely exposed to free environment.

In an embodiment a patient table or seat, which may have any construction and is denoted with numeral 2, is generally associated to the magnetic unit. Several embodiments of the patient table or seat are possible. According to one embodiment, the patient table or seat 2 may have a structure adapted to form closable housing compartments, as is schematically shown in FIG. 1. According to other embodiments the patient table may be in the form of a movable table having wheels and/or combined with elevator means and/or combined with means for changing the configuration of the table and/or a table having at least one table plate which is tiltable in order to be oriented along several directions, such as for example in the tables for carrying out weight bearings examinations.

The magnetic unit or structure, with the components listed above, is associated to control, monitoring and processing units, which have the function to control and adjust the various components of the magnetic structure and to receive and process echo signals to extract therefrom all data useful for the reconstruction thereof into an image formed by an array of light image dots, the so-called pixels, whose brightness and/or colour are univocally related to the received data and whose position is related to the position, within the body part under examination, wherefrom the echo signal was transmitted.

According to an embodiment the MRI system comprises an electronic unit 3 for controlling the signal exciting and receiving devices, a unit 4 for entering commands to the signal exciting and receiving unit, a display and image processing unit 5 and a filing and storage unit 6 are associated to the magnetic unit.

In the present embodiment of FIG. 1, the unit 3 for controlling the signal exciting and receiving devices is at least partly contained in the case of the magnetic unit 1 and/or possibly also at least partly contained within the structure of the patient table 2, in one part thereof 202, for instance a support column, having the form of a switchboard.

The units for entering commands 4 to the signal exciting and receiving units, for display and image processing unit 5 and for filing and storage 6 are included, partly as hardware peripherals and partly as software programs, in a traditional personal computer.

The communication between the unit 3, contained in the case of the magnetic unit and/or in the structure of the patient table, with the units 4, 5, 6 of the control console provided by the personal computer is obtained by means of a communication bus denoted with numeral 7.

The communication bus may be of any type, e.g. a conventional communication bus of the Ethernet type, of the SCSI or USB type or of any other type, which allows multiplex communication among several units.

Once the type of bus to be used is selected, the implementation of interfaces with the bus 7 on the individual units 3, 4, 5, 6 is well-known in the art.

The above electronic units may be formed by specific developed boards which circuits are dedicated to carrying out the specific tasks or by generic hardware which comprises processors configured to carry out program instructions which enables the generic hardware to carry out the specific tasks.

Electronic units may be produced according to several techniques available for the construction of electronic boards and circuits.

Different programming languages and operative systems may be employed for generating the control programs providing the processors to execute the instructions for carrying out the specific tasks, such as for example Windows NT® based program languages or similar.

Figure 2:
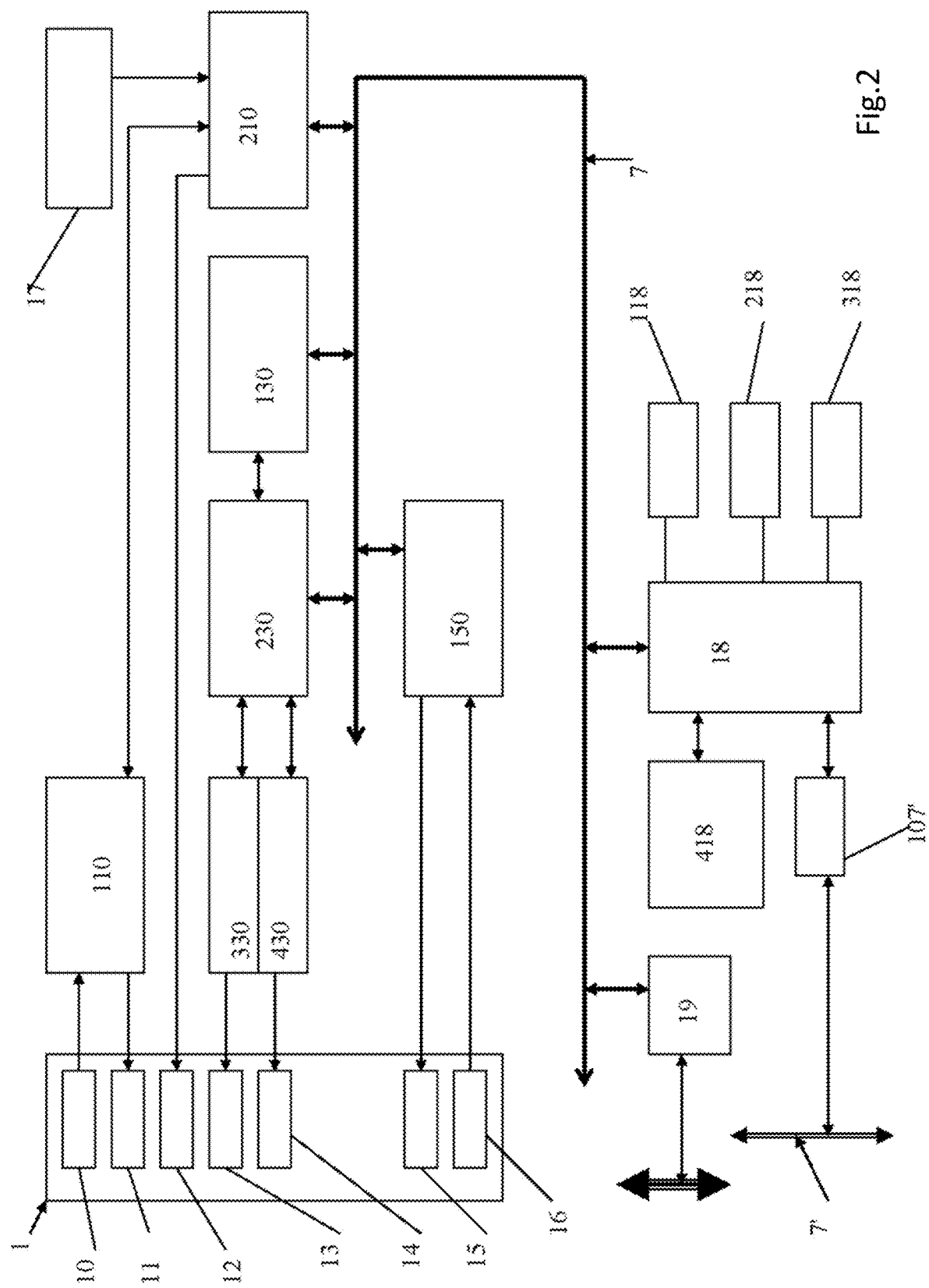
FIG. 2 is a more detailed block diagram of an embodiment of an MRI system according to the present invention.

FIG. 2 shows a block diagram of a higher level embodiment of the generic embodiment of FIG. 1. In this embodiment, the magnetic unit 1 includes several components, as shown in the figure, that is, in addition to static field generating magnets, temperature sensors 10, heating and/or cooling means 11, at least one compensation coil 12, at least one transmission or excitation coil 13, one or more gradient coils 14, tuning means 15 and at least one receiving coil 16, as well as one or more magnetic field sensors 17.

The temperature sensors and the heating and/or cooling means are controlled by a temperature control unit 110 which includes means for reading the signals of the sensors 10 and means for supplying the heaters and/or coolers 11, which are controlled by a thermal control unit 210 based on the actual detected temperature and on the comparison thereof with the preset nominal values.

The thermal and magnetic control unit also controls the compensation coil 13 to correct the static magnetic field with reference to the variations induced therein by external magnetic fields and based on the actual field values detected by the magnetic field sensors 17. A supervision, pre-processing and reconstruction unit 130 controls a data capture and control unit 230 which in turn controls the amplifiers 330 and 430 for the signals provided to the transmission or excitation coil 13 and to the gradient coil/s 14 respectively. A receiver unit 150 is responsible for tuning 15 the receiving coil 16 and identifying the receiving coil 16, as well as for receiving the data collected by said receiving coil 16.

According to an embodiment these units are all contained wholly or at least partly inside the case of the magnetic unit, and/or wholly or at least partly in a closable compartment of the structure of the patient table. According to a further embodiment these units may be all or at least partly formed by a traditional PC running a program in which instructions are coded for controlling the PC processor or processors in order to carry out the functions of the said part of units.

According to an embodiment, the supervision, pre-processing and reconstruction unit 130, the control and data capture unit 230, the thermal and magnetic control unit 110 and the receiver unit 150 communicate with one another and/or with other units by means of a bus 7.

More particularly, these units communicate with the CPU 18 of a conventional personal computer, having conventional peripherals, according to the desired or required quantity and type. The display and command entry peripherals denoted with numerals 118, 218, 318, as well as a mass memory for filing and a memory for the specific image processing and display software, collectively denoted with numeral 418 are connected to the CPU 18.

According to another embodiment, the CPU 18 may also communicate 107' in turn with a local communication network 7', such as a LAN network within the hospital or an Intranet or Internet network, or a network of any other suitable type. The communication bus 7 is also connected with a modem unit 19, which allows connection to a local network and/or to other machines connected to the local network via a telephone line. This redundancy, besides allowing to communicate with local networks in other locations, is also an alternative method for connection with the local LAN network, in case of temporary communications problems of the network interfaces.

As is apparent from the above description, the communication bus is not only provided between the individual units, but is also extended inside the latter, thereby providing the greatest configuration and operation freedom as well as allowing to add functional units with new functions and/or to replace old type units with more modern units. Replacement operations, both for upgrading and repairing purposes are apparently easy. As long as signals are encoded consistently with the bus in use, any unit may be connected to the communication bus 7 and is able to exchange data and commands with the other units.

The above disclosed exemplary construction of the apparatus allows additional configurations, which might be highly advantageous in terms both of cost effectiveness and of organization and management. In fact, the connection of various units through a conventional data bus allows to control several apparatuses, even of different types, but all having the same configuration as the processing and control electronics, from a single location or from a limited number of locations.

According to a further embodiment, a system may be also provided which comprises several machines organized in groups, each having a single dedicated console in the form of a conventional computer, each conventional computer associated to each group being configured as a client computer, which accesses a server computer via a network. In this case, the server computer may contain many different programs for controlling image acquisition and/or processing and reconstruction procedures, e.g. a database of Nuclear Magnetic Resonance imaging sequences, a database of signal filtering and/or processing procedures aimed at modulating the definition and/or the contrast and/or the signal-to-noise ratio and/or the imaging times, whereas the client computers may access the server databases to extract programs and/or image acquisition and/or processing procedures from said databases.

By this arrangement, client computers may be configured in a more inexpensive manner, especially as regards memories and graphic sections. Also, limited-quality means, e.g. monitors or printers, may be provided locally, while higher-quality means are associated to the server. This provides considerable resource savings, and allows, for instance to purchase higher-quality monitors and/or other display means, such as printers or the like.

Figure 3:
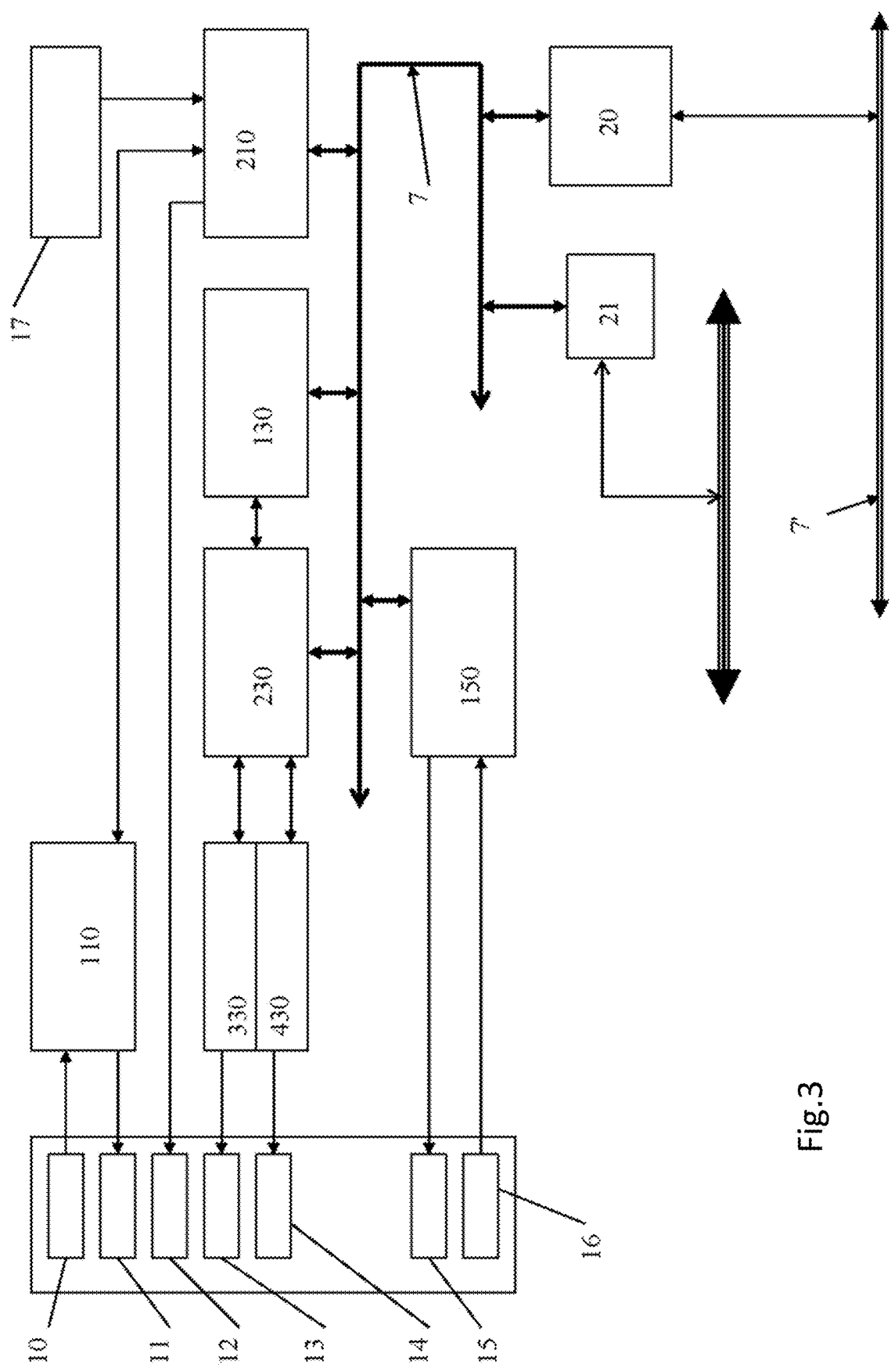
FIG. 3 illustrates a block diagram to a further embodiment of the MRI scanner according to the present invention.
Figure 4:
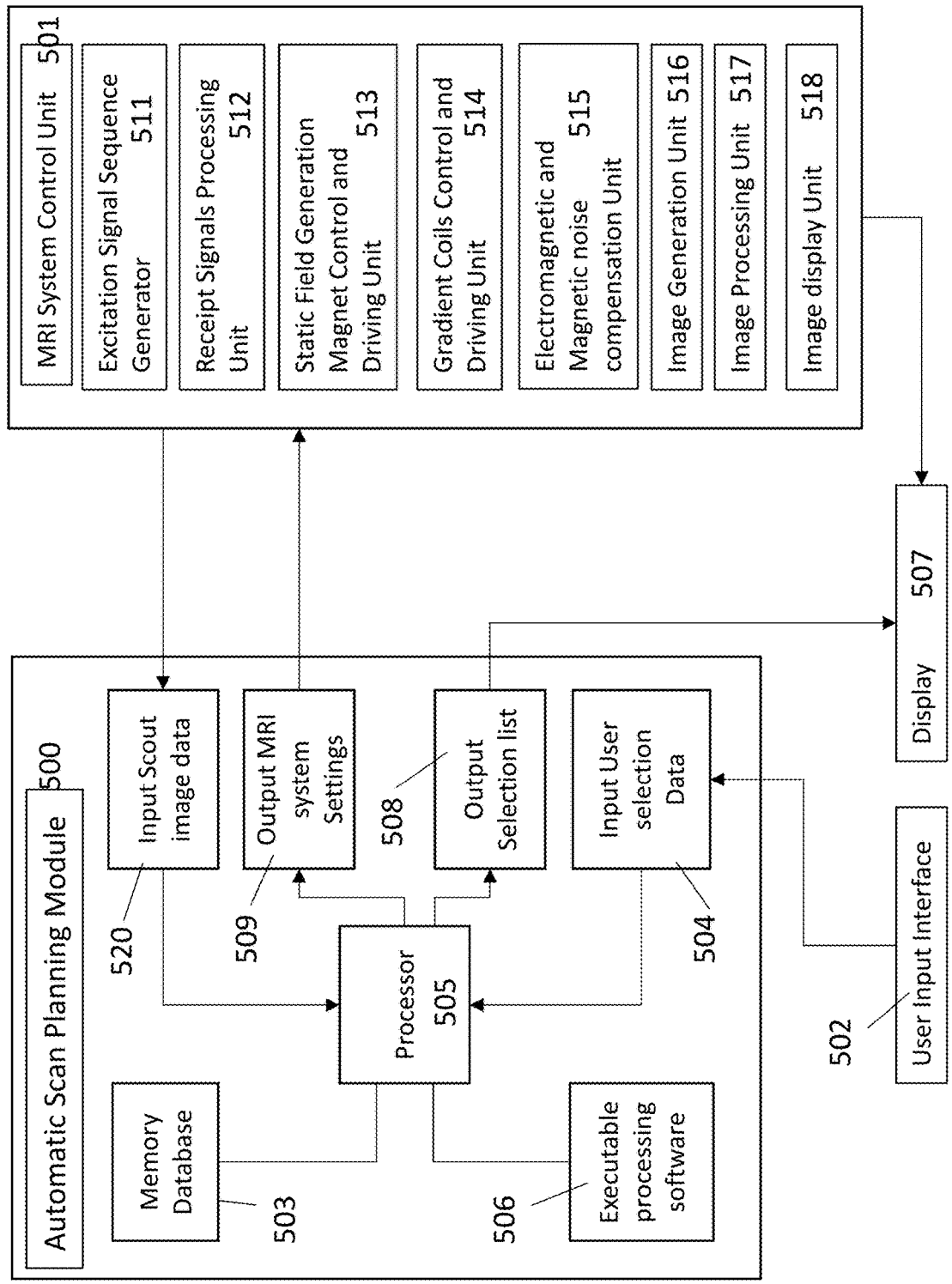
FIG. 4 is a block diagram of a further embodiment of the MRI system according to the present invention.

A further configuration example of an MRI system according to the invention, fit for this configuration, is shown in FIG. 3. Same functions or means in this figure are denoted with same numerals. As is evident from the comparison with FIG. 2, the units that are expressly dedicated to the control of the magnetic unit and to the reception of echo signals, as well as to signal processing to extract image data are identical to those described with reference to FIG. 2. However, unlike the previous example of FIG. 2, the apparatus has no dedicated console, but includes a local CPU unit which controls the communications between the internal bus 7 and the communication bus, e.g. a LAN network or the like, denoted with numeral 20. A modem 21 may be provided to allow communication via telephone lines. The local CPU 20, whereto local memories may be associated, accesses a local computer via the LAN network, which local computer integrates the units as described in FIG. 2 and is designed to control several machines. As mentioned above, the local computer may in turn be a client computer of a server computer for generally controlling several groups of apparatuses. The presence of an internal controlling CPU 20 does not cause a real cost increase, both due to the comparatively little cost of CPUs and to the fact that this configuration allows to reduce the number of computers dedicated to the control of machines.

Moreover, according to a further embodiment, the local CPU may be used to also control local peripherals, such as storage, display, print and control entry means.

It shall be noted that the presence of a local CPU 20 does not even hinder the possibly desired provision of one or more machines having a dedicated console.

Figure 5:
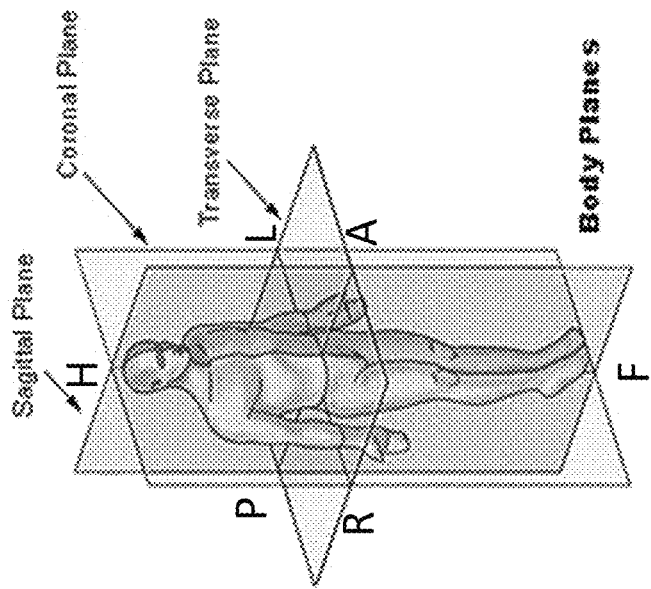
FIG. 5 illustrates schematically the three orthonormal anatomical planes.

FIG. 5 illustrates a block diagram of an embodiment of the automatic scan planning module which selects and applies automatically the proper setting of parameters for carrying out the examination, i.e. the imaging scan.

In the embodiment of FIG. 5 the automatic scan imaging module is indicated by 500 and the MRI system with 501. A user interface 502 allows the user to specify before starting with the image acquisition session and to input user defined or selected MRI image acquisition settings.

Particularly the user input interface 502 is configured to input by the user a selection of the kind of examination, the automatic scan planning module configures the MRI. A memory 503 is configured to store a database of the different kind of examination to be carried out which are univocally identified by an ID and which ID is associated to at least one factory pre-defined optimum combination of settings of the image acquisition parameters of MRI system corresponding to the selected specific kind of examination. In combination with the settings of the image acquisition parameters also specific image acquisitions protocols may be factory defined and stored in the database and correlated to one or more examination kinds. These settings may be determined theoretically or experimentally and empirically according to data collected and processed by the System producer in order to continuously update and optimize the settings on the base of the increasing knowledge experienced by use.

The automatic scan planning module 500 comprises a interface 504 for receiving the Input User selection data relative to the examination kind and received by the User input interface 502. A processor 505 which executes an automatic scan planning control program stored in a memory 506, prints on a display 507 the selection list of possible imaging acquisition parameter settings and/or protocols correlated to a selected examination kind via an output interface 508 for the said selection list of possible imaging acquisition parameter settings and/or protocols correlated to a selected examination kind.

The database relating the examination kinds and the one or more factory pre-defined image acquisition settings or protocols of the MRI system may be in the form of a look up table stored in the memory 503 to which the processor 505 and the executable control software 506 executed by the processor 5050 have access.

When only one setting of image acquisition parameters or only one image acquisition protocol is possible, since only one of these setting of parameters or one protocol is provided in the database for a selected examination kind, the processor 505 controlled by the executable processing program 506 shows the said parameter setting and/or protocol on the display 507 and also automatically applies the said settings to the MRI system 501 by sending setting control signals to the MRI system control unit 501.

If more than one setting of the image acquisition parameters or more than one imaging protocol is possible for a selected examination kind, the automatic scan planning module 500 displays the list of the said settings and/or protocols on display 507 for selection of one of the said settings or protocols by the user through the user interface 502. Upon input of the selection of one of the possible settings and/or protocols, the automatic scan planning module 500 configures the MRI system automatically with the image acquisition settings corresponding to the selected specific kind of examination through the output interface 509 of setting control signals 510 transmitted to the MRI system control unit 501.

According to the present embodiment, the MRI system control unit 501 may be provided with a processor configured to execute a MRI system control program which configures the processor as a controller of control and driving units of one or more of the MRI system specific operative units necessary to be configured and driven for carrying out the specific kind of examination selected by the user.

According to the example of FIG. 5, The MRI system control unit 501, controls by means of a non-illustrated processor executing a control program one or more of the following specific driving or control units of the operative units or organs of the MRI system such as: an excitation signal sequence generator 511, a Receipt signals processing unit 512, a static field generation magnet control and driving unit 513, a gradient coils control unit 514 an electromagnetic and magnetic noise compensation unit 515 and image processing units such as an image generation unit 516 reconstructing image data from the received signals which are coherent with the representation of the structural and/or functional information coded in the received signals about the imaged object, image processing unit 517 for carrying out image optimization, recognition, segmentation, evaluation processes on the image data and an image display unit 518 transforming the image data in control signals for driving a display 507 so to reproduce the information coded in the image data in visual representation of the object scanned.

According to an embodiment, the automatic scan and planning module may be a fully hardware unit, a combination of hardware and software unit. In one embodiment the hardware unit is in the form of specific hardware configured for carrying out a specific task. Operation may be implemented in the hardware configuration or in an hardware/software embodiment the hardware is an operation dedicated hardware which carry out operation specific software such as a firmware, allowing to have some flexibility in the function which may be carried out by the hardware.

According to a further embodiment the automatic scan planning module may be in the form of a software in which the instructions are coded for driving a processor 505 in order to carry out the functions of one or more of the units 502, 503, 504, 5050, 506, 507, 508, 509. The processor and peripheral hardware may be a generic programmable hardware such as a PC or similar which is also destined to execute other programs for configuring the processor and the related peripheral to carry out other functions of operative units of the MRI system, such as for example the MRI system control unit 501 and of one or more of the controller or driving units 511 to 518.

For example, the processor and the associated peripherals can be one or more of the processors disclosed in the embodiments of FIGS. 1 to 3.

According to a specific function of the automatic scan planning module which is related to the automatic positioning and orientation of one or more slices of the object under examination along which images has to be acquired and which example will be described in greater detail in the following description. The automatic scan planning module has also an interface 520 with the MRI system control unit 501 for receiving scout image data, relating to a scout image acquisition scan carried out before starting the parameter setting or protocol selection session according to the automatic method of the present invention. In this example, the user can directly select and start the acquisition of a scout image of the object and the results of the scout image are fed to the automatic scan planning module for carrying out an automatic definition of the position and orientation of slices along which the images have to be acquired in the imaging session based non anatomic or other references in the scout images and on the examination kind selection made by the user and on the setting of the scan parameters and/or of the imaging protocols related to the selected examination kind.

Figure 6:
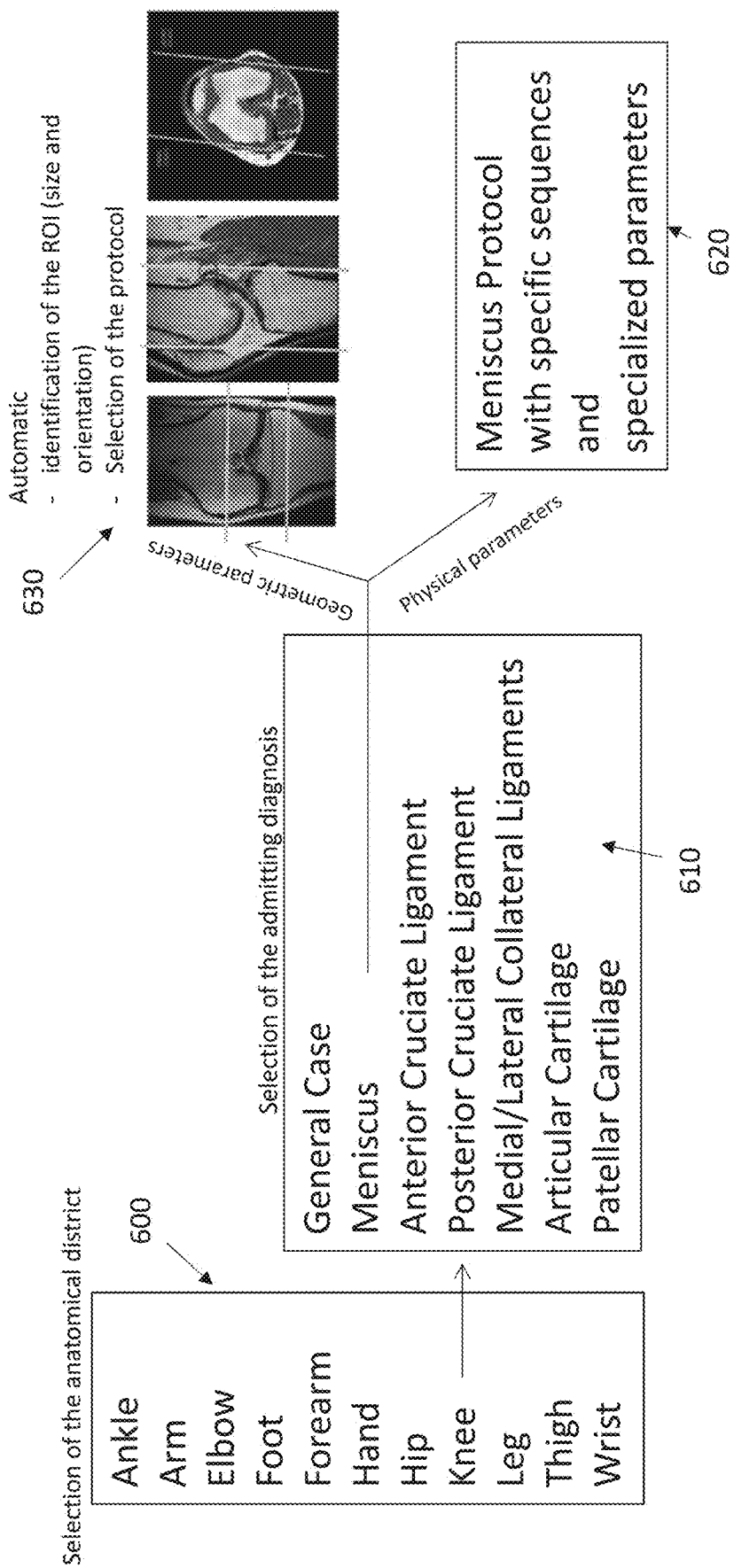
FIG. 6 illustrates a user interface for controlling the imaging parameter setting according to the present invention.
Figure 7:
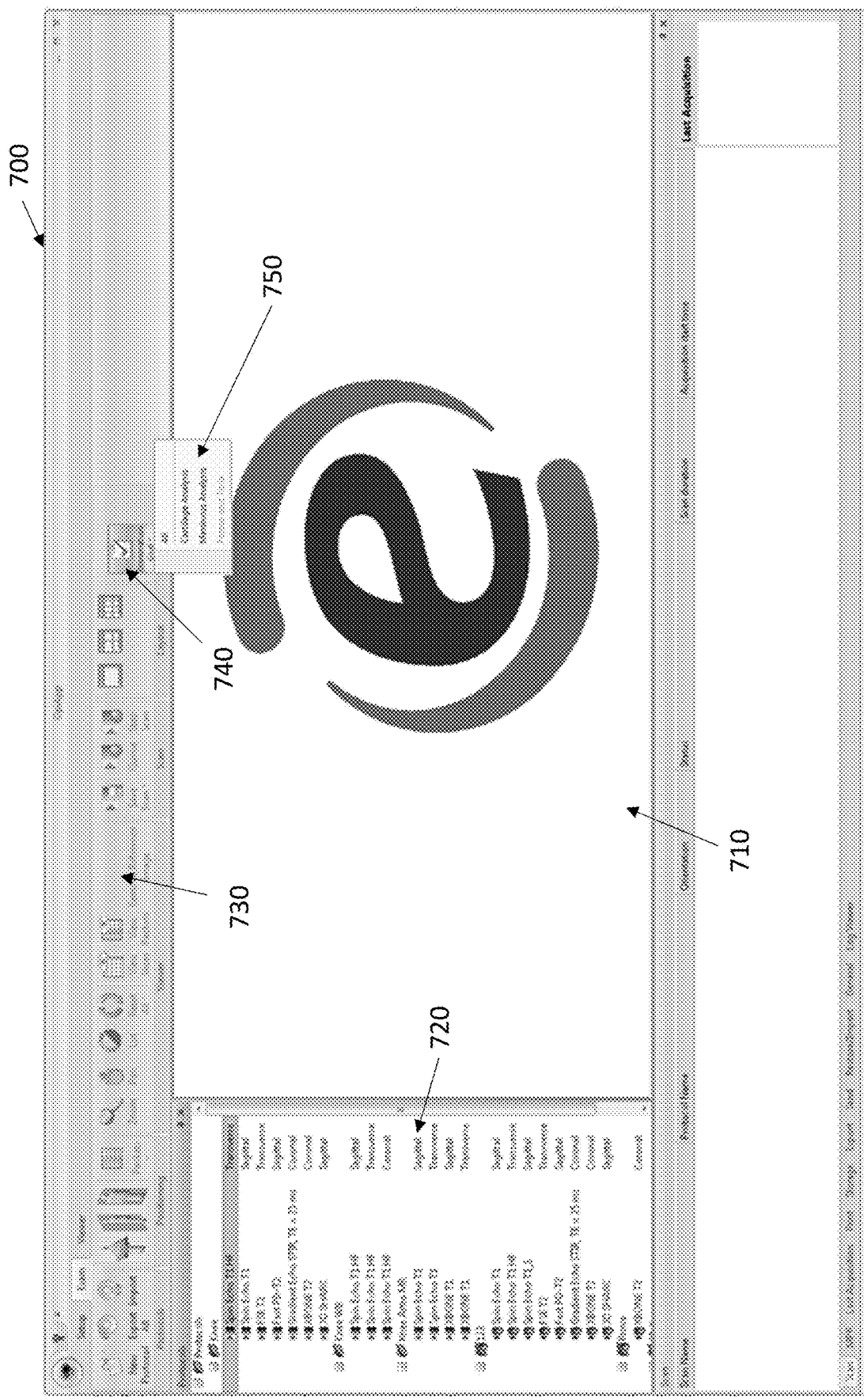
FIG. 7 illustrates a window interface displayed by the system in executing a software for carrying out the method according to the present invention.
Figure 20:
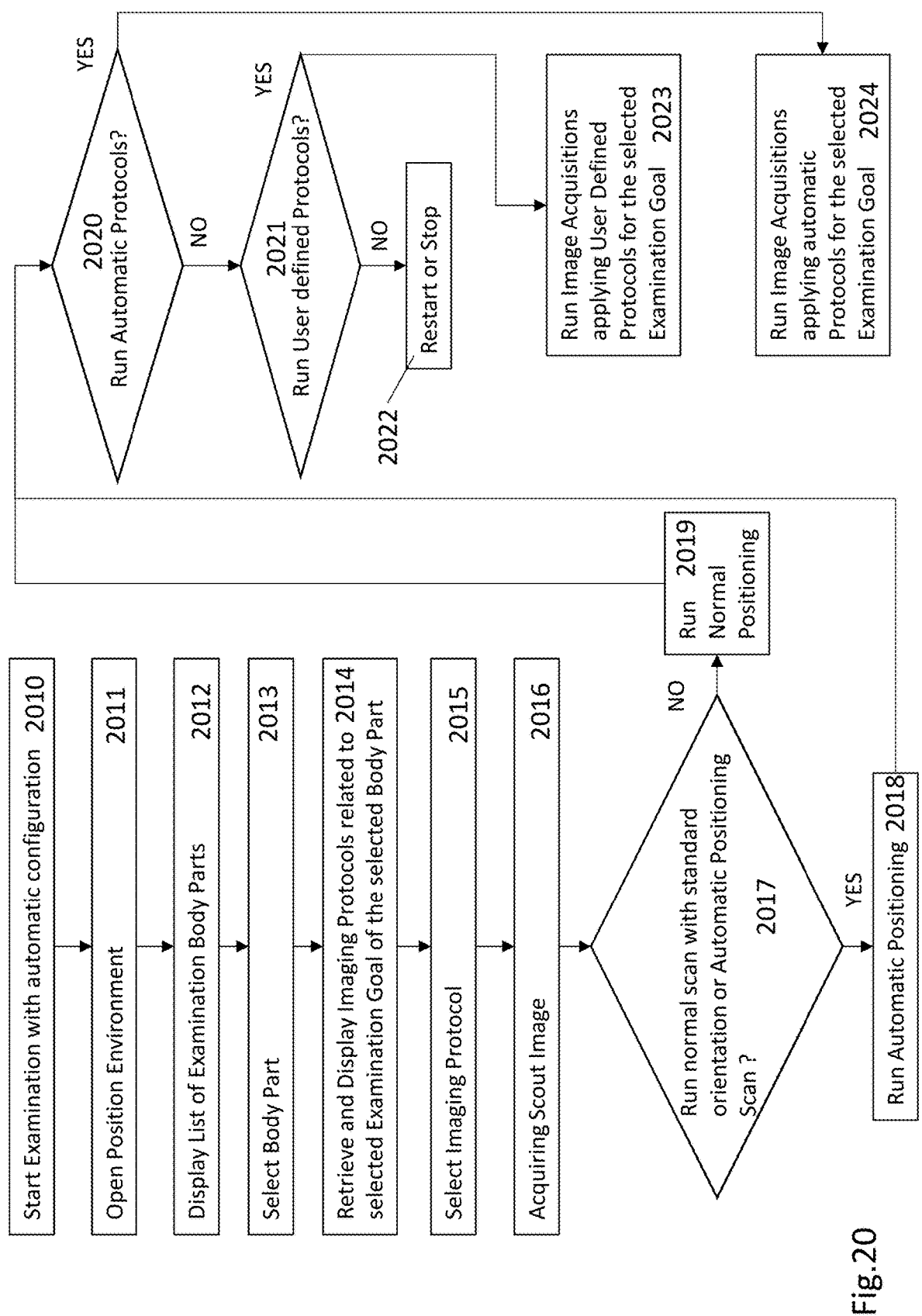
FIG. 20 is a flow diagram of a generic embodiment of the method according to the present invention.

FIG. 6 shows a functional diagram of a user interface an example of which is shown in FIG. 7 and for carrying out the steps of an embodiment of the method according to the present invention represented with the flow diagram of FIG. 20.

According to the embodiment of FIG. 6 the step 600 allows the selection by the user of an anatomical district in a list of anatomical districts as indicated by 600. Using for example a point and click kind of selection interface like the one usual in the PC systems, the user can select an anatomic district which in this case is for example chosen as the knee. Clicking on the selected anatomical district determines that the interface shows a list 610 of available imaging parameter settings and/or protocols suitable for the diagnosis of specific part of the knee or of a general purpose imaging parameter setting and/or protocol. Each anatomic part for which a specific setting of the imaging parameters and/or for which a specific imaging protocol is available can be selected and addressed by a pint and click user input. In the present case the Meniscus is selected. Clicking on the selected voice of the list 610, has as a consequence that the automatic scan planning process is started by addressing in the database for example the one stored in the memory 503 of the embodiment of FIG. 5, and determines the available imaging parameter settings and/or protocols related to the selection of the available diagnosis. According to the description of the embodiment of FIG. 5 if only one setting is available for imaging the meniscus the setting is applied automatically to the MRI system. If more than one setting is available a further selection list will be visualized and offered for selection to the user in the user interface.

According to the example of FIG. 6, the settings or the protocols may include settings relating to physical parameters, i.e. parameters relating to the physics of the imaging process and geometric parameters. Physical parameter settings 620 like specific meniscus imaging sequences and other specialized parameters are used for configuring automatically the specific units of the MRI system according to one or more of the system architectures of FIGS. 1 to 4. Geometric parameters mainly relate to the automatic identification of the ROI in relation to size and orientation in space such as in defining the position and orientation in space of the slices along which the one or more images of the knee focalized on the diagnosis of the meniscus have to be acquired.

The graphic appearance of the interface may be chosen according to any kind of design. FIG. 7 shows a windows designed interface. A window 700 which is according to the typical and user windows interfaces is printed on screen. A central area 710 is dedicated to visualizing the images acquired. A lateral left area 720 shows automatically the list of available parameter settings and/or protocols related to the selected anatomic district (in this case the knee) and to the specific diagnosis for which the imaging is carried out (in the specific case the Meniscus diagnosis).

The selection of the kind of diagnosis is selectable by the knob 740 on a toolbar 730. Selecting the knob by a mouse or a touch interface opens the menu 750 showing the diagnosis available for the meniscus. Selecting one of the two voices of the menu starts the automatic scan planning process and in the left hand area 720 the available protocols and or settings are listed as a root diagram which allow the user to also manually select the protocol and or setting and also to modify the fabric-defined protocol or setting.

The flow diagram of FIG. 20 shows an embedment of the steps to be carried out in starting the automatic scan planning process. At step 2010 by using for example a knob of the graphic interface, for example in the embodiment of FIG. 7 an activation knob (not shown in detail) on the toolbar 730, the examination with automatic MRI system configuration is started.

As a first step 2011 the position environment of the scan process is opened for determining the position and orientation of the slices along which the images of the object has to be acquired. The execution of the process provides at step 2012 the display of the list of body parts for which examination is possible for example the list 600 of the embodiment according to FIG. 6. Selection a body part at 2013 the automatic scan planning module 550 executes the step 2014 of retrieving and displaying the protocols related to selectable examination goals available for a selected body part. Selection at 2015 of an imaging protocol triggers automatically the acquisition of a scout image at step 2016.

Upon acquisition of a scout image which is carried out by using usual settings of the system, the user can chose at 2017 if he wants to run the imaging scan using the standard manual orientation and positioning of the slices of the object along which the images has to be acquired or if an automatic positioning is desired. Depending on the choice either a normal positioning process is carried out as indicated by 2019 or an automatic positioning is carried out as indicated by 2018.

A further choice is presented to the user relating the possibility to choose at step 2020 between running an automatic defined imaging protocol or setting or a user defined imaging protocol or setting as indicated at step 2021. If for both selections the answer is no the process is either aborted or restarted as indicated by the step 2022. Choosing to run an automatic protocol or setting will start an image acquisition process for which the automatic scan planning module automatically configures the MRI system applying to it the protocols and or settings related for the selected examination goal as indicated by step 2024.

If a user defined protocol or setting has to be applied the image acquisition is carried out by applying this protocol and this setting to the MRI system as indicated at step 2023.

FIGS. 8 to 19 show different embodiments of a specific case of the method according to the present invention which relates specifically to the automatic positioning and orientation of image slices in relation to a selected anatomic district and a general or diagnosis specific image acquisition parameter setting and/or imaging protocol. In the present example the specific anatomic districts is the knee and the method will be described in relation to a general purpose imaging and a specific diagnosis purpose consisting in the imaging of the meniscus for diagnostic aims.

Figure 8:
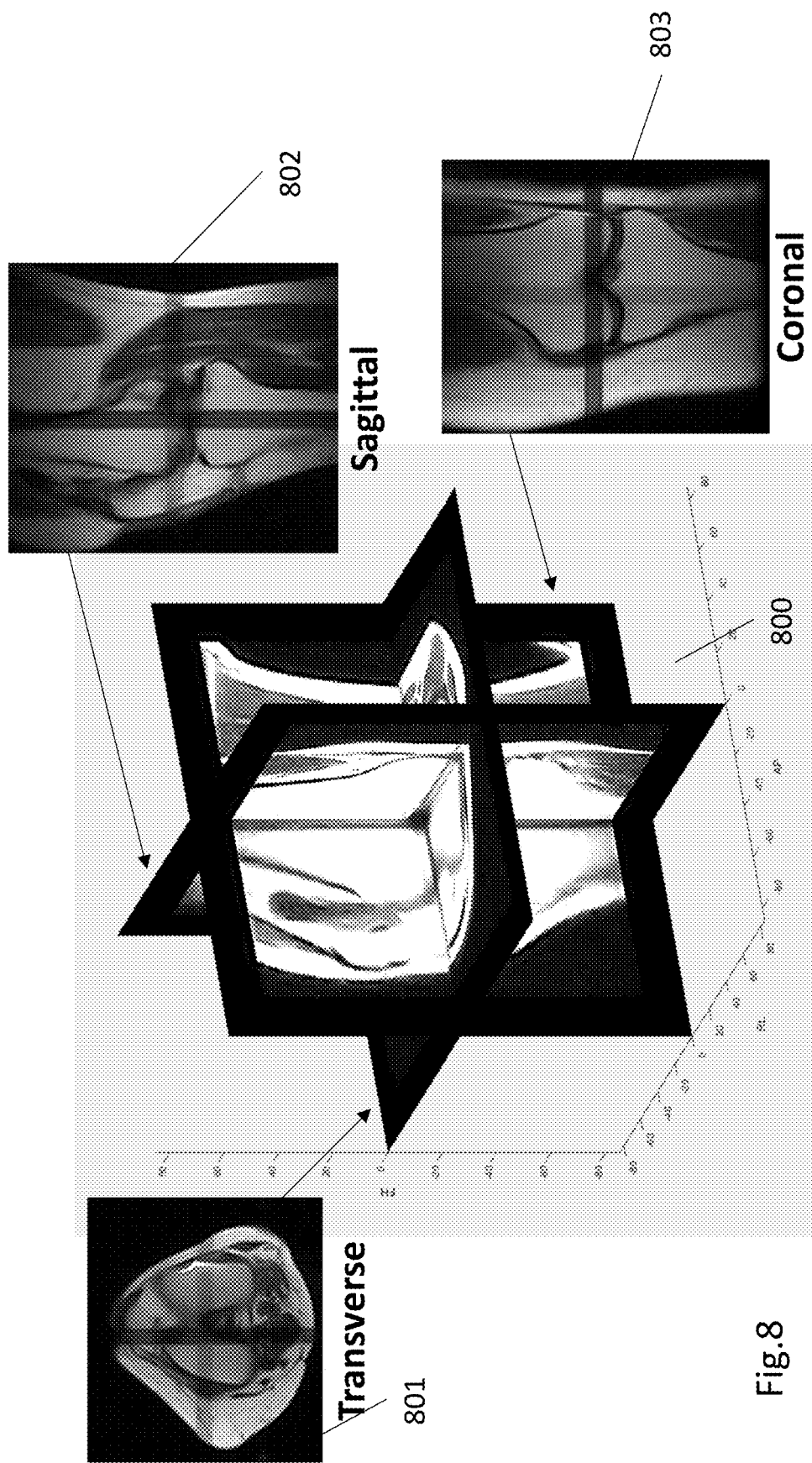
FIG. 8 illustrates the results of a 2D scout image acquisition of the anatomic district of the knee.

As described in the previous generic embodiment of the method in accordance with FIGS. 6, 7 and 20, a scout image is acquired. The scout image can be a three dimensional image or as in the method of the present embodiment a two dimensional scout image. This two dimensional scout image consists in at least three images along three characteristic orthonormal anatomic planes as defined according to FIG. 5. The results of the scout image acquisition are represented in FIG. 8. In which the central image 800 shows the knee and the relative position of the three orthonormal anatomic planes in relation to a knee. The single images on each of the three orthonormal planes are shown in FIGS. 8 and 801 indicates the image along the transverse plane, 802 the image along the sagittal plane and 803 the image along the coronal plane.

According to an automatic scan positioning and orientation of the slices along which images have to be acquired in relation to the specific anatomic district, the specific diagnosis purpose and the specific imaging parameter setting and/or imaging protocol, the scout image data of the object under examination are used by the automatic scan planning module in order to infer the initial positioning settings for the current scan. According to an embodiment the automatic scam planning process shall always give the opportunity to the user to change the positioning parameters which were automatically determined according to the diagnostic needs. This can be done during the course of the imaging process in the phase in which the settings of the MRI system and/or the protocols for imaging are chosen and applied or in a further variant embodiment this can be done also in a dedicated system configuration phase in which the user can launch a configuration management software allowing to generate User defined parameter settings and/or imaging protocols. This user defined parameter settings and/or protocols may be stored in the database of factory preconfigured imaging parameter settings and/or protocols and correlated to one or more anatomic districts and to one or more examination goals such as diagnosis purposes.

According to an embodiment, the factory preconfigured imaging parameter settings and/or protocols are generated by analysing in a factory executed generation process several imaging parameter settings of the MRI system and/or imaging protocols by evaluating the images obtained using the said settings and/or protocols in carrying out imaging on real cases and/or on phantoms. The evaluation of the results allows to generate imaging parameters settings and/or protocols based on a wide experience and which are a combination of several variants in order to obtain an optimized setting of the parameters or an optimized protocol. This knowledge based generation of the setting of the imaging parameters and of the protocols may be continuously updated and the updated databases may be rendered available as an upgrade of the automatic scan planning units of existing MRI systems which may be installed in the memory of the MRI system for example in the memory 503 of the automatic scan planning module 500 of the embodiment according of FIG. 6. The database may be available for download by the MRI system from a download server or the updated database may be read from a portable memory device where it is stored by providing the MRI system with a corresponding reader, for example using USB drives as storage substrate and an USB input port on the MRI system, or by storing the database on a CD or DVD configured as read-only memory or as a RAM memory which is read by a corresponding CD and DVD reader on the MRI system.

According to an embodiment, the factory preconfigured imaging parameter settings and/or protocols related to the automatic positioning and orientation of image slices filtered by the anatomic district and the examination goal consist in a model of image slice orientation and position determined relatively to a scout image model.

According to an embodiment the said model of position of slices and orientation of slices is determined by using references on the scout images which may be of any kind. According to a variant embodiment the said references may be external markers which are applied to the anatomic district or internal markers or anatomic references of the object imaged in the scout image and which references can be clearly recognized.

According to an embodiment the process of automatic positioning and orientation of slices along which the images have to be acquired and which position and orientation is determined by defining the orientation and position with reference of the scout image is carried out by applying an algorithm which applies the slice position and orientation of the factory predetermined model of imaging slice position and orientation to the scout images acquired for the object under examination.

According to an embodiment this is carried out by detecting the references on the scout image acquired for the object under examination and apply a transformation of the said scout images in order to realign the said references with the same references on the scout image/images on which the imaging slice position and orientation model has been determined.

Since according to the embodiment providing a two dimensional scout image the three orthonormal anatomic planes are related one to the other, the model of the factory preconfigured imaging slice position and orientation is called a bounding box orientation.

Figure 9:
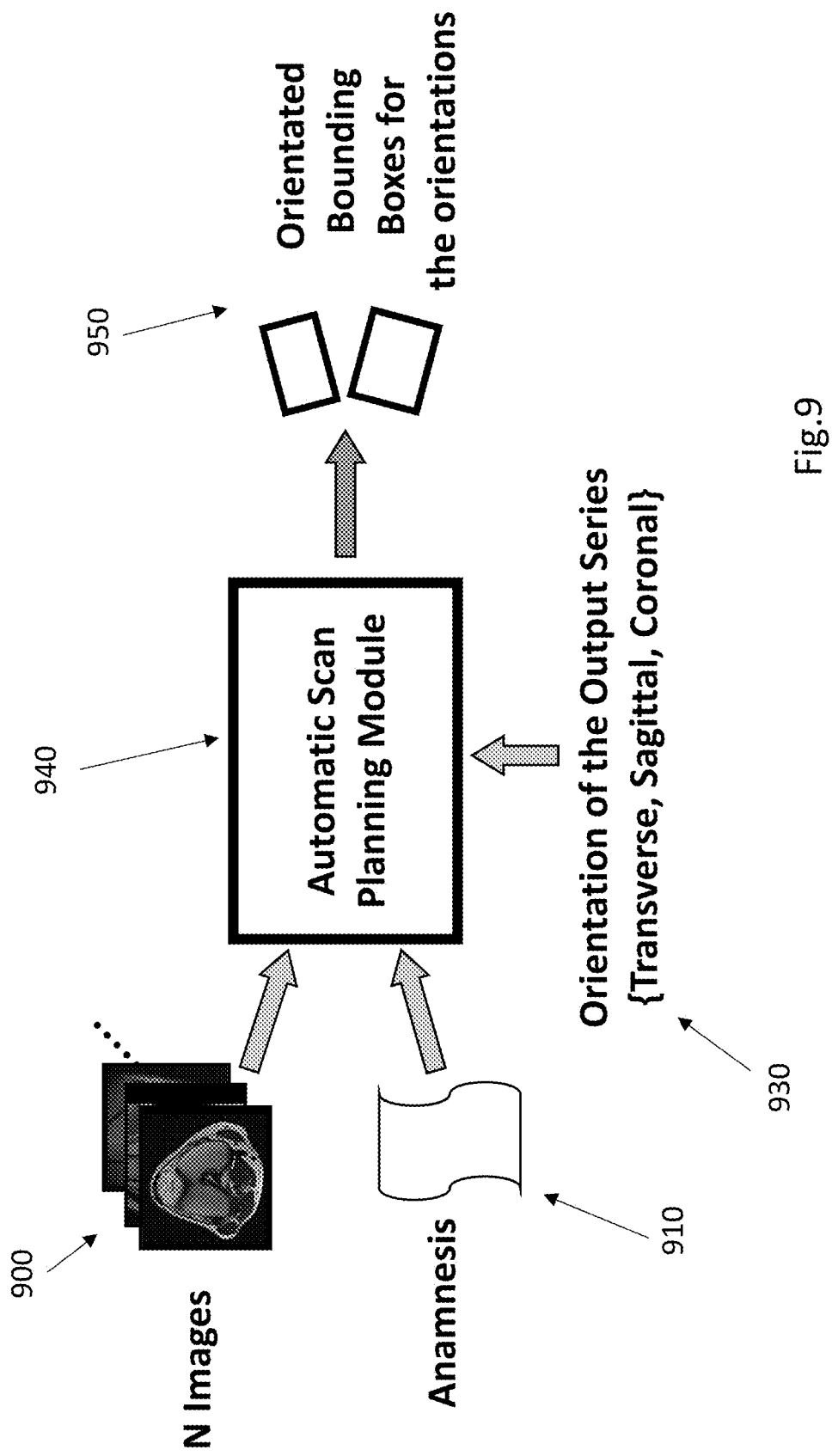
FIGS. 9 and 10 illustrate a functional diagram of two embodiments of the method according to the present invention.
Figure 10:
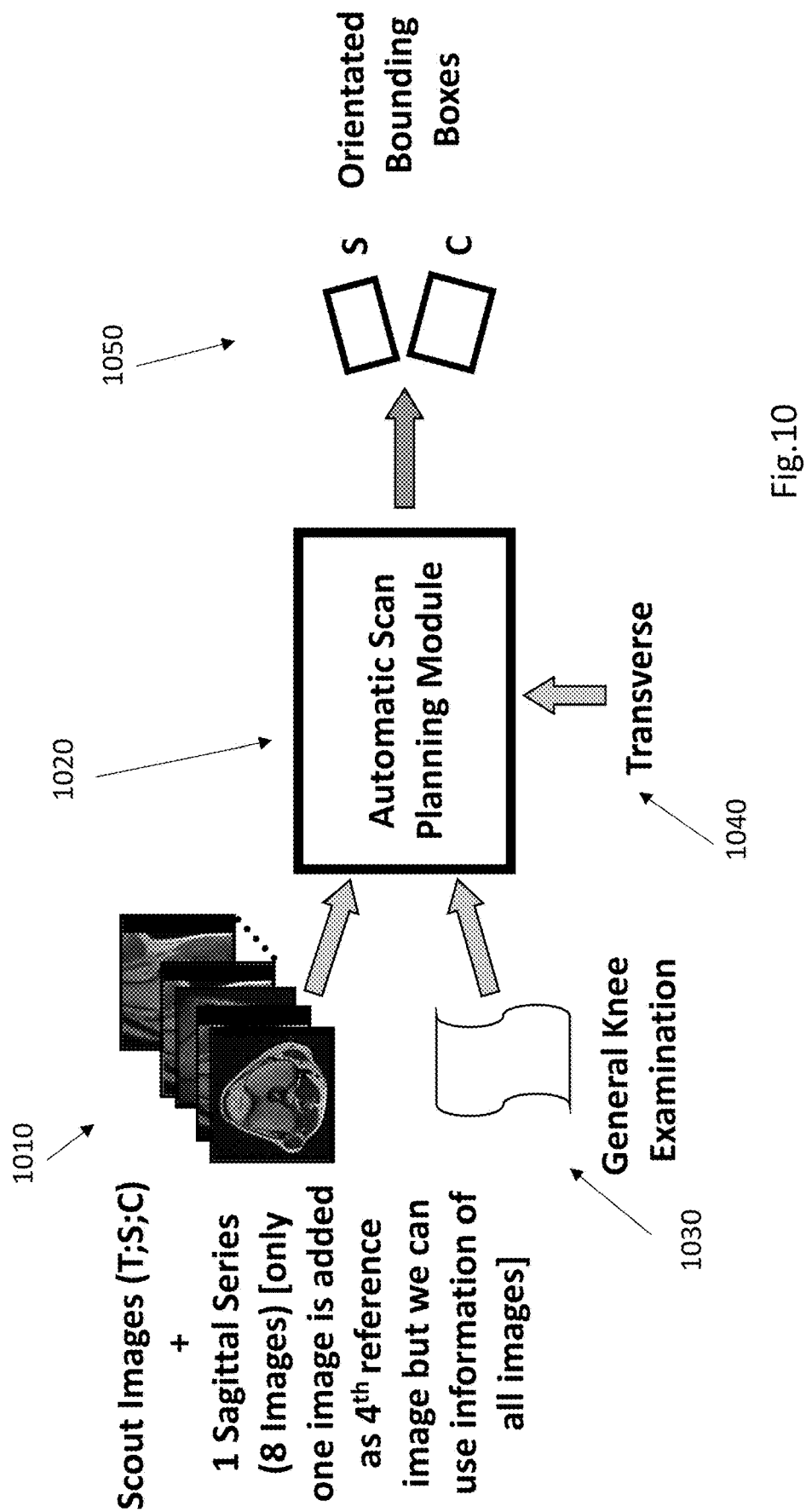

FIGS. 9 and 10 show with a diagram the process of applying the factory preconfigured position and orientation model.

According to the embodiment of FIG. 9 at step 900 a number N of scout images along the three related orthonormal anatomic planes are fed to the automatic scan planning module. The region to which the images refer is determined by the type of examination which defines the anatomic district and the diagnosis related examination type as indicated by the step 910. The automatic scan planning module is set to determine one or more position of the slices along a certain orientation as indicated by the step 930. This data is analysed by an automatic scan planning module 940 which applies the model of automatic positioning and orientation of the slices along which images have to be acquired related to a scout image of a specific anatomic district and a specific examination goal or type and configures the MRI system to acquire images along the slices at the position and along the orientation defined by the model as indicated at step 950.

In the embodiment of FIG. 10 a special case is shown related to a general knee examination. In the input 1010 at least the three scout images along the three orthonormal anatomic planes of the anatomic district of the knee are fed to the automatic scan positioning module 1020. The anatomic district of the knee and the kind of examination defined here as general examination is set at step 1030. More than one image may be fed. The request of the user is to have a series of transverse images of the knee for a general purpose diagnostic examination kind as the step 1040 shows. The automatic scan planning module 1050 applies the model to the said images and determined the slice orientation and position of the sagittal and coronal slices.

Figure 11:
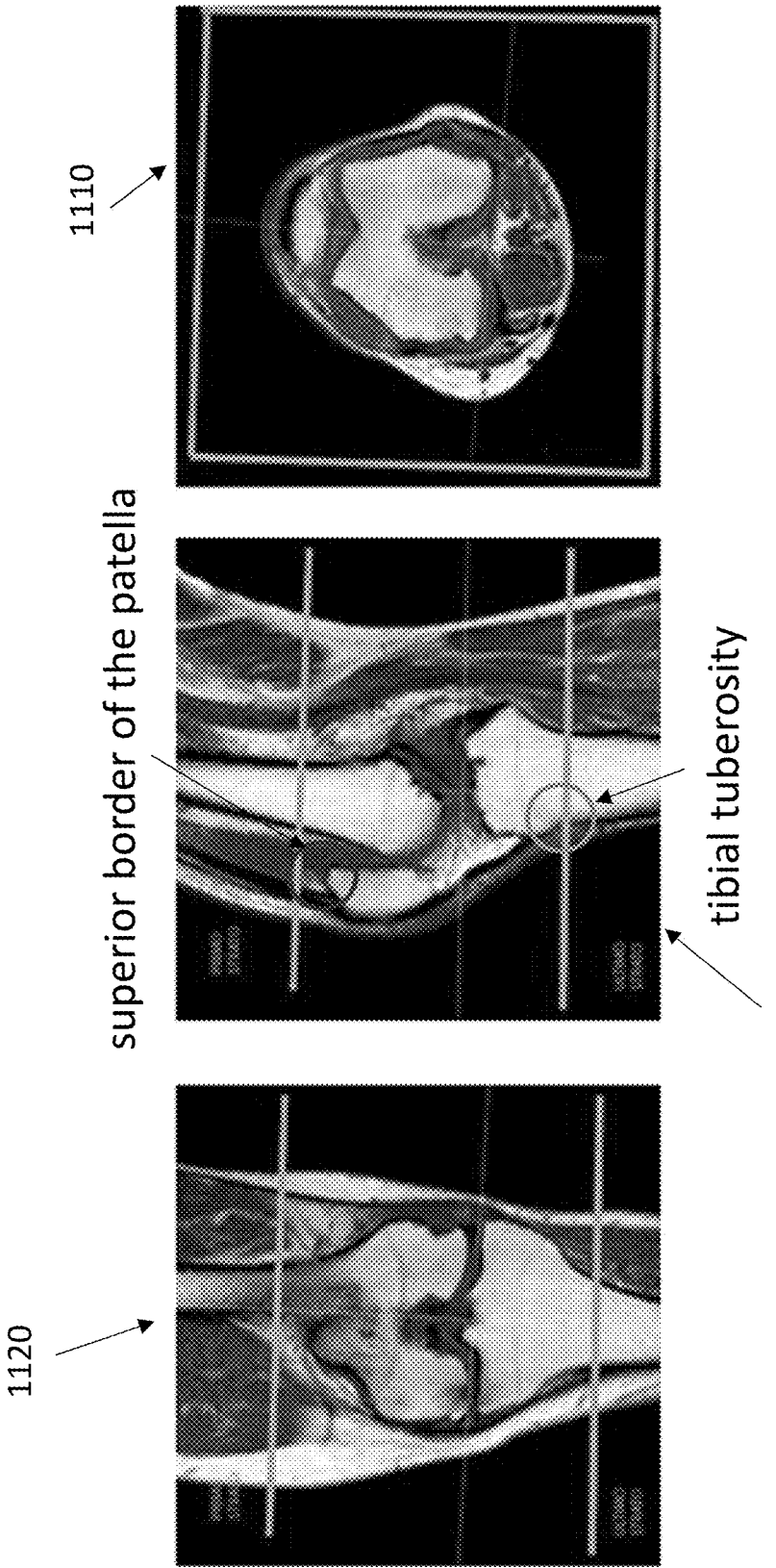
Figure 13:
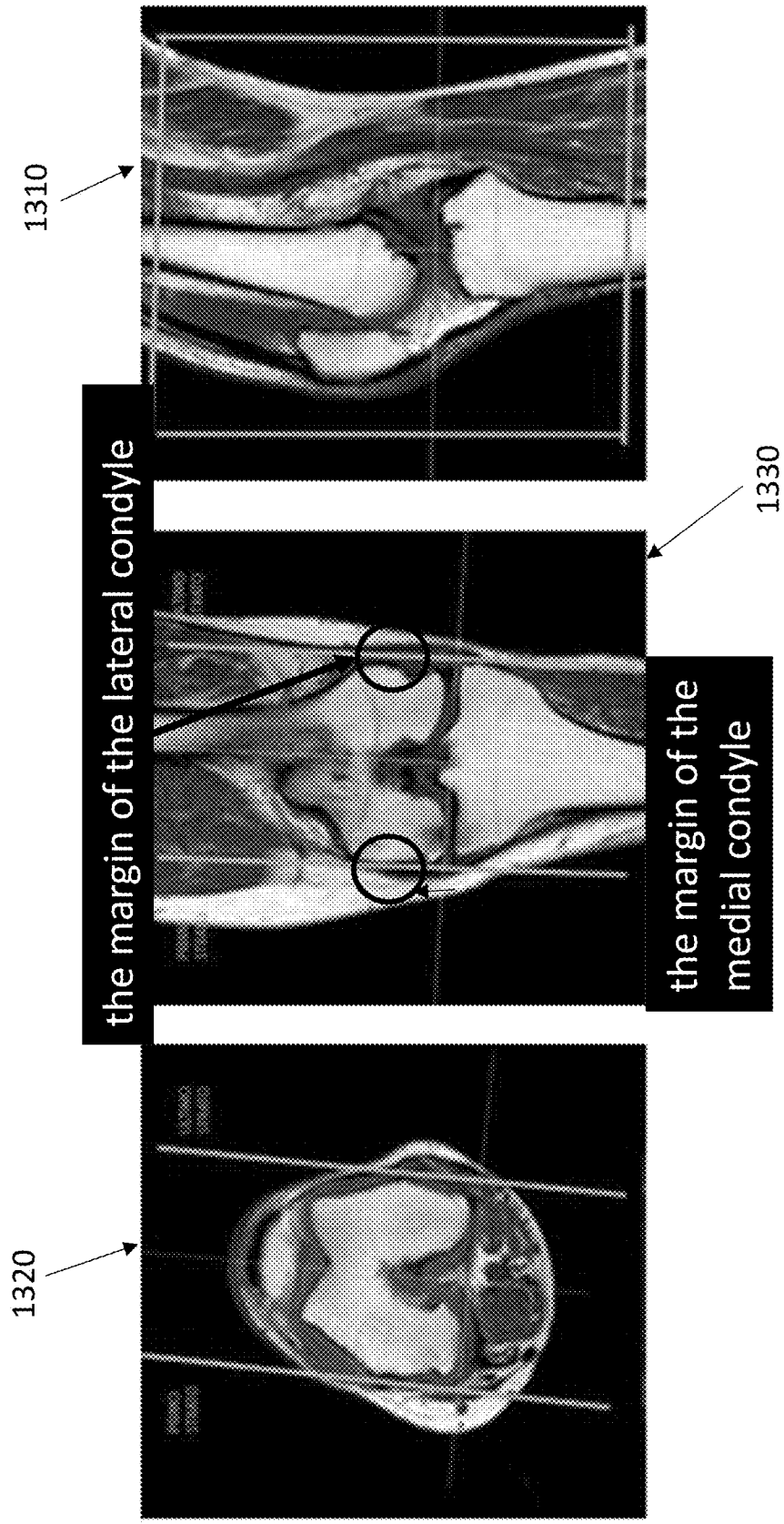

The FIGS. 11 to 13 show the positioning model and the anatomic references for the anatomic district of the knee in relation to a generic diagnostic purpose and for the positioning on each of the three orthonormal anatomic planes. In FIG. 11 the positioning of the transverse slice 1110 is shown in the sagittal and coronal images 1020 and 103. The two anatomic references for the positioning of the transverse slice limits are indicated as the superior border of the patella and the tibial tuberosity. In FIG. 12 the positioning of the coronal slices as indicated with 1210 is defined in the transversal and coronal planes 1220 and 1230 the two limits of the coronal plane are indicated by the lines touching the anatomical district of the posterior margins of the femur condyles and the posterior margin of patella. In an analogous way as for the two previous positioning examples, for the positioning of the sagittal slice 1310 the limits of the said positioning are determined in the transversal and coronal planes as the lines passing through or being secant to the anatomic references of the margin of the lateral condyle and the margin of the medial condyle.

Figure 14B:
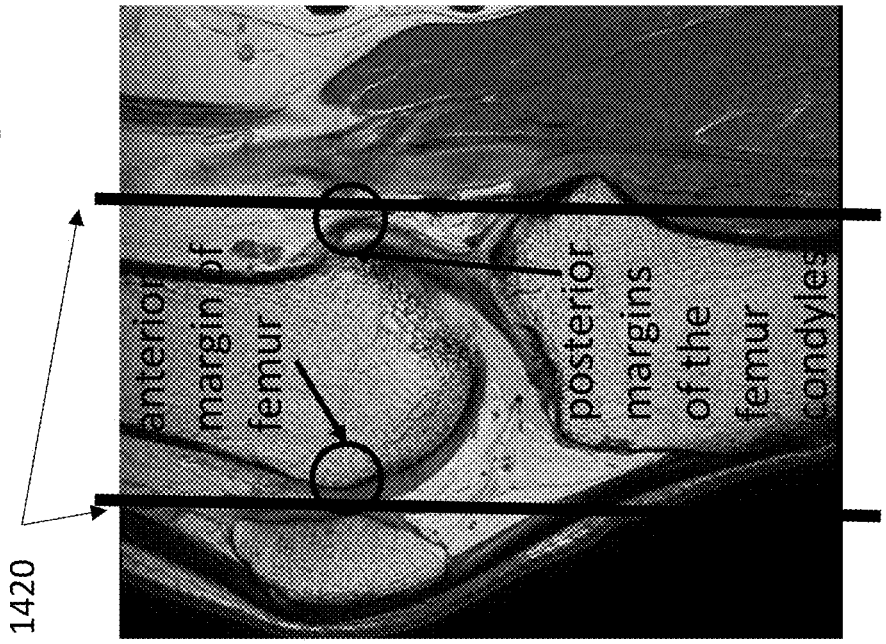
FIGS. 14a, 14b and 15 illustrate the images obtained by means of automatic positioning of the slices related to the anatomic district of the knee and to the diagnosis of the meniscus.
Figure 14A:
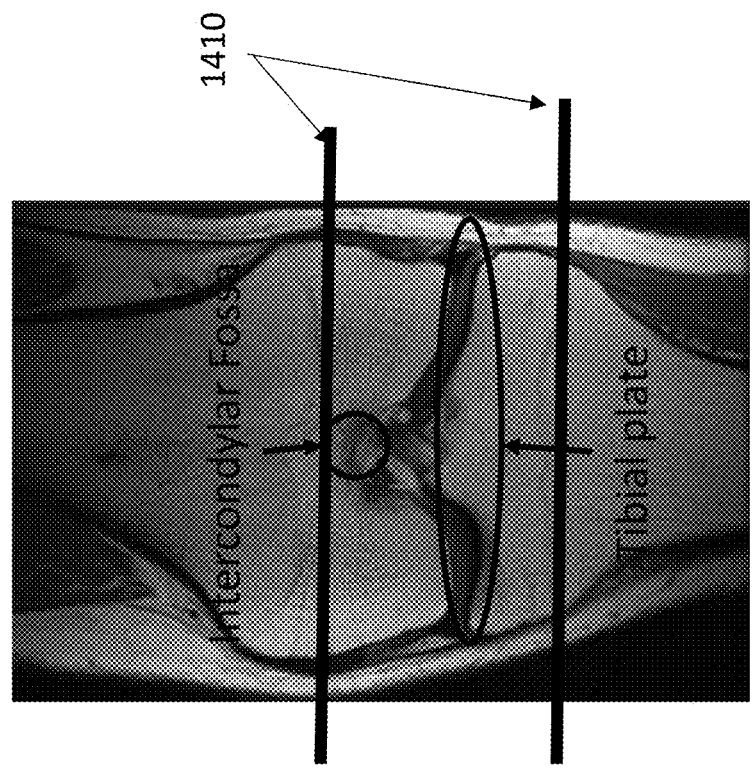
Figure 15:
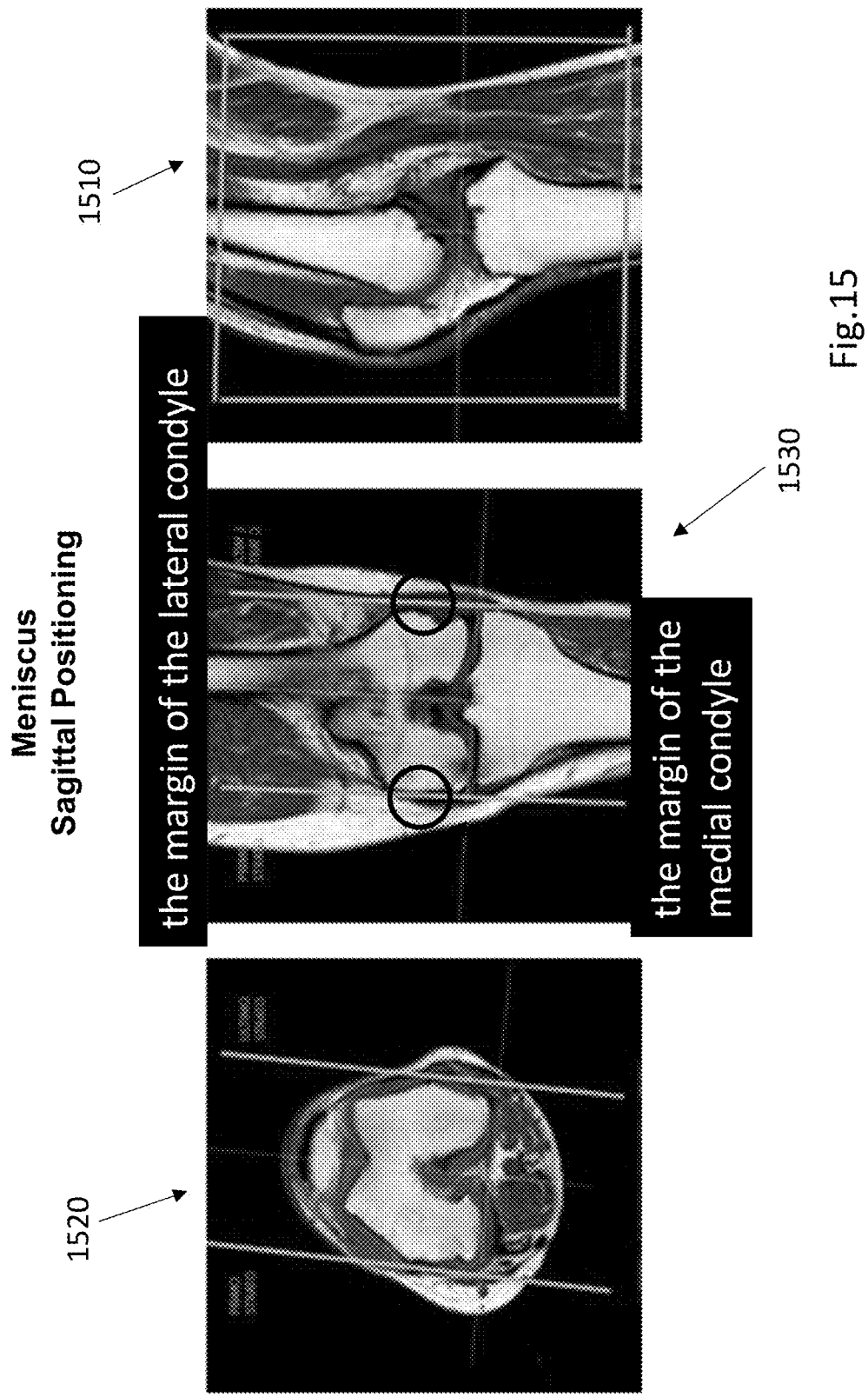

FIGS. 14 and 15 show similarly the limits for the positioning respectively of the transverse slice, the coronal slice and of the sagittal slice and the corresponding anatomic references for the specific examination type related to the meniscus.

In FIG. 14a, the anatomic references are the intercondylar Foss and the Tibial plate. Here the lines 1410 represents the transversal plane orientation in relation to the image which is along the coronal plane. In FIG. 14b the coronal positioning is represented in the image along the sagittal plane. The lines 1420 represents the coronal plane position at respectively one of the two anatomic references being identified as anterior margin of femur and posterior margin of the femur condyles.

FIG. 15 shows in a similar way to FIGS. 11 to 13 the sagittal positioning in the case of diagnostic imaging of the meniscus. In the images 1510 and 1530 of the transverse and coronal orientation the anatomic references are the margin of the lateral condyle and the margin of the medial condyle. The result of the image slice along the sagittal orientation is indicated by numeral 1510.

According to the above example the limits determined by the position of the orthonormal planes within certain limits indicated in the images along the other orthonormal planes defines as a first result the region of interest which has subjected to imaging in relation to examination type selected by the user. This has a result also that the number of slices parallel to the orthonormal plane must be sufficient to cover the anatomic region delimited by the positions of the said orthonormal planes between the two positions defined by the anatomic references. So in relation to FIG. 11, the ROI is the region of the knee comprised between the superior border of the patella and the tibial tuberosity and the number of slices parallel to the transverse plane must cover this ROI. In relation to FIG. 12, the ROI is the region of the knee comprised between the posterior margin of the patella and the posterior margins of the femur condyles and the number of slices parallel to the coronal plane must cover this ROI. In relation to FIG. 13, the ROI is the region of the knee comprised between the posterior margin of the lateral condyle and the margin of the medial condyle and the number of slices parallel to the sagittal plane must cover this ROI. In relation to the special case of the meniscus, the relating to FIG. 14a, the ROI is the region of the knee comprised between the intercondylar fossa and the tibial plate and the number of slices parallel to the transversal plane must cover this ROI; referring to FIG. 14b, the ROI is the region of the knee comprised between the anterior margin of the femur and the posterior margins of the femur condyles and the number of slices parallel to the coronal plane must cover this ROI; referring to FIG. 15, the ROI is the region of the knee comprised between the margin of the lateral condyle and the margin of the medial condyle and the number of slices parallel to the sagittal plane must cover this ROI.

FIG. 16 shows a table of steps of the parameter settings relating to slice orientation and positioning.

On the left a list of steps is shown and on the right the graphic representation of the said steps is illustrated.

According to the embodiment of FIG. 16 the method provides for a chamfer matching of the scout images with a model 1610. In three phases 1620, 1630, 1640 the scout images according to the coronal plane, to the sagittal plane and to the axial plane are aligned with the model 1610. The alignment steps of each phase comprises a model scaling in order to rescale the model in relation to the scout images or vice versa, and a translation step of the model according to pre-set translation distances and pre-set translation directions and pre-set translation steps as it appears from left side of FIG. 16. The axial alignment provides also for a rotation step around the z-axis for a pre-set angular distance and with pre-set rotation steps.

Figure 17:
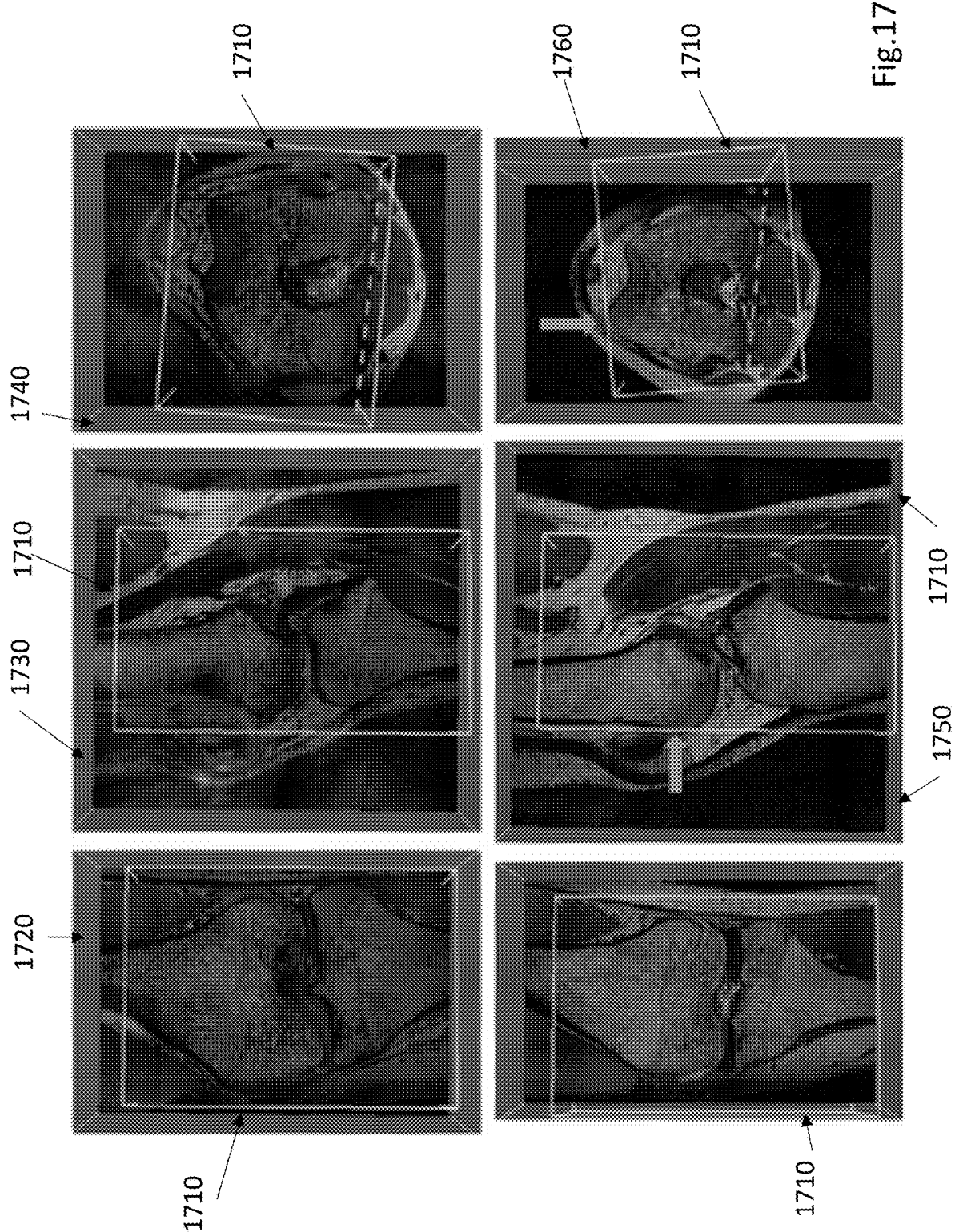
FIG. 17 shows the results of the automatic positioning of the slices in a case according to the present invention and in the case of failure of a manual selection.

FIG. 17 shows the results of the three alignment steps.

The upper three images show the oriented bounding boxes 1720, 1730, 1740 respectively for the coronal, sagittal and axial view. The model or bounding box limits 1710 in all the three images appears to be well aligned with the anatomic references and to enclose in an optimal way the ROI for each view.

The lower row shows a bade result of a positioning in which as indicated by the arrows in the images relating to the sagittal and axial views 1750, 1750, the ROI defined by the bounding box is not well aligned with the anatomic references and particularly in this case with the condyles, so that the knee joint is not completely covered in the anterior parte and on the lateral side the covered area is too large.

Figure 18:
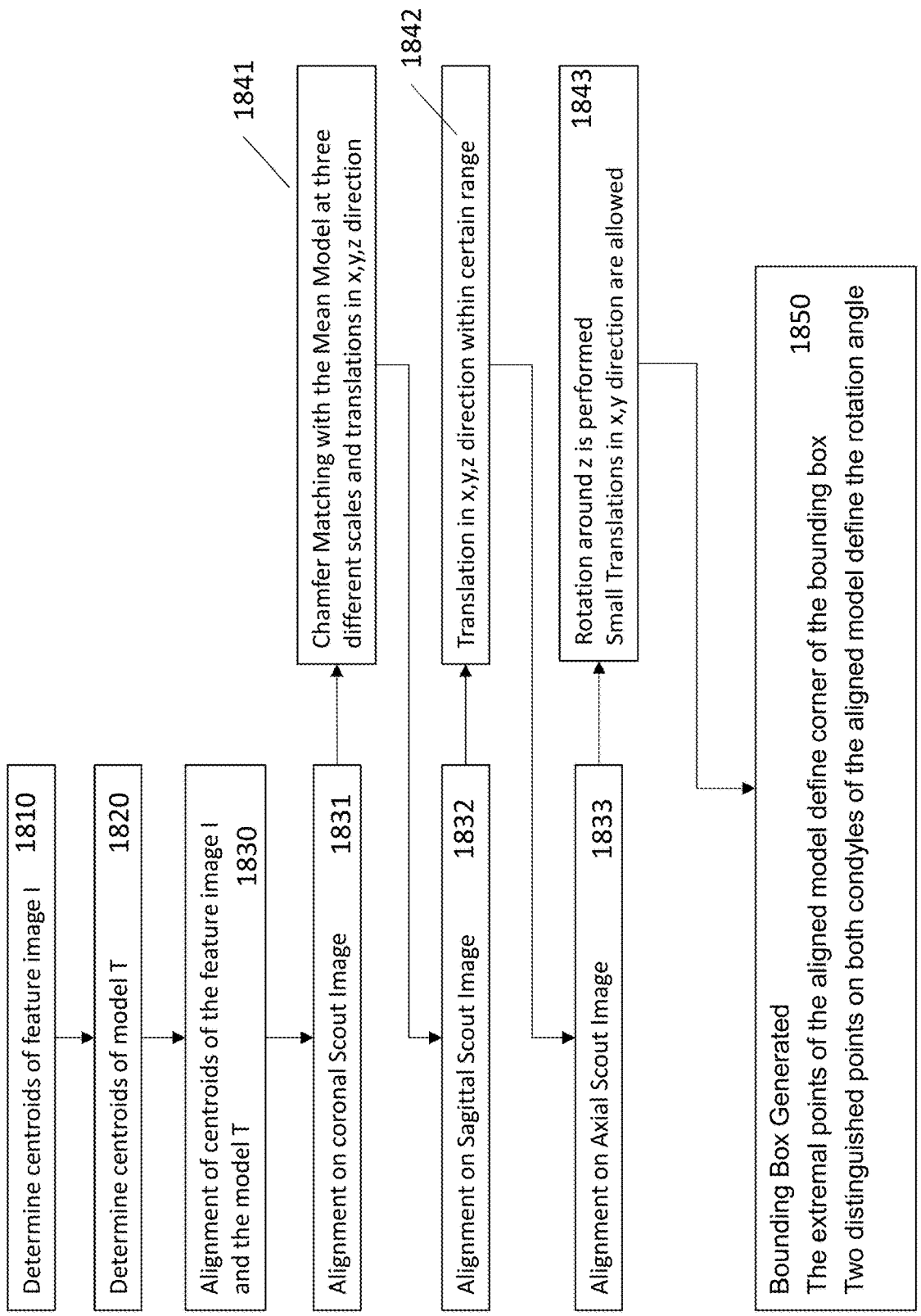
FIG. 18 is a flow diagram of an embodiment of the method for automatic positioning and orienting the image slices.

The flow diagram of FIG. 18 relates to an embodiment of an algorithm for carrying out the chamfer matching of the example of FIG. 16. The feature image I is the scout image of the object under examination, while the model image is the model image according to the factory predefined positioning and orientation model. At steps 1810 and 1820 the centroids of the said feature image I and of the model image T are determined. At step 1830 the centroids of the feature image I and of the model T are aligned by carrying out a first alignment step 1831 of the coronal scout image. This is carried out according to step 1841 executing a chamfer matching with the model at three different scales and with translations of the model in the x, y and z direction. Step 1841 is followed by step 1832 consisting in the alignment of the sagittal scout image with the model consisting in the translation 1842 in the x, y, z direction of the model in relation of the sagittal scout image within a certain defined range of maximum translation. Step 1833 provides of the alignment of the axial (i.e. transversal) scout image comprising a rotation 1843 around the axis z and if necessary a small translation within a translation range of predetermined dimension in the x and y direction. The result 1850 is the generation of the bounding box defining for each orientation (coronal, sagittal and transverse (i.e. axial) the limits of the ROI to imaged and being represented in FIG. 17 as a three dimensional parallelepipeds 1710. The external pints of the aligned model define the corners of the bounding box and two distinguished point on the condyles of the aligned model define the rotation angle.

Figure 19:
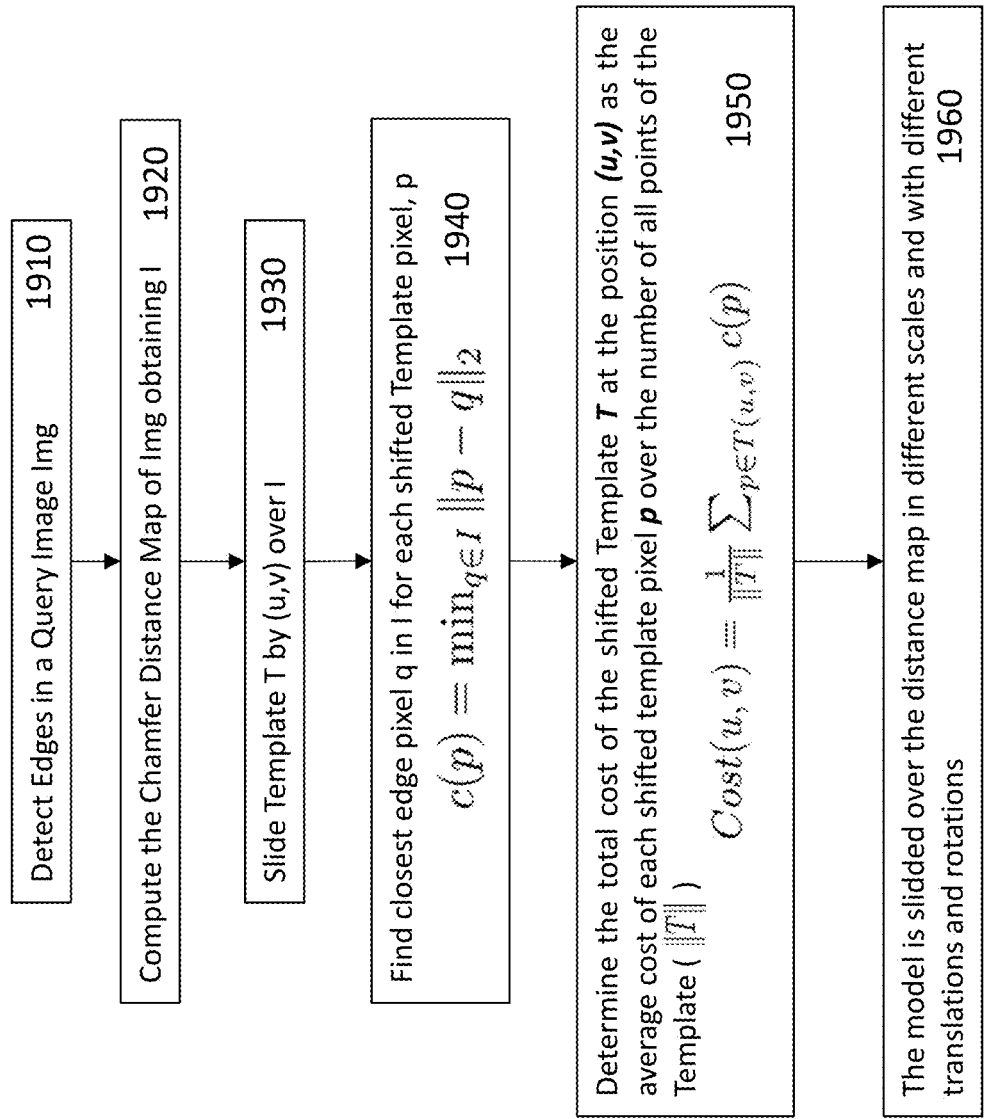
FIG. 19 is a flow diagram of the algorithm for processing the images in order to identify and register anatomic references for applying template position and orientation of image slices to the scout images of the object to be examined.

According to an embodiment the algorithm for carrying out the translation comprises the steps of the flow diagram of FIG. 19.

The steps of the algorithm provides for detecting the edges in a query image Img 1910. Computing at step 1920 a chamfer distance map of query image Img obtaining an image I. Carrying out a step 1930 of sliding the template image T over image I along the coordinates (u,v). At step 1940 find closest edge pixel q in image I for each shifted Template pixel p according to the equation $$c(p) = \min_{q \in J} \|p - q\|_2$$

Where c(p) closes edge pixel; I: matrix of pixel of image I p, q, pixels of image I and of template T. Step 1950 determines the function defining the criterion of determining the alignment result in form of the cost function. Which describes the total cost of the shifted template as the average cost of each of the shifted templates.

$$\text{Cost}(u, v) = \frac{1}{\|T\|} \sum_{p \in T(u,v)} c(p)$$

Where $\|T\|$ is the template and p are the pixels of the template; u,v are the position coordinates of the template. For alignment the model is moved over the distance map in different scales and with different translations and rotations as indicated at step 1960.

The invention claimed is:

1. An MRI system comprising:
a cavity for accommodating a target body under examination or a part thereof;
a magnet for generating a static magnetic field in a volume of space;
gradient coils for generating gradient magnetic fields in addition to the static magnetic field according to three spatial directions;
a hardware processor configured to drive and control the gradient coils and the magnet;
a transmission antenna connected to an excitation signal sequence generator for transmitting spin echo excitations signals into the cavity housing the target body;
a receipt antenna for receiving the MRI signals caused by the excitation signals;
the hardware processor further configured to process the MRI signals and extracting image data information and for generating images;
a display for displaying the generated images;
the hardware processor further configured to manage the excitation signal sequence generator and the display;
the display configured to enable a user to input MRI image acquisition settings to be specified by the user before starting with an image acquisition session;
an automatic scan planning module comprising a memory in which a look up table or a database of examination specific settings of the MRI system is stored respectively associating a specific kind of examination with a factory pre-defined and empirically determined combination of settings of the MRI system, the said automatic scan planning module controlling the display to display a list of alternative specific examinations and providing a selection organ for the user, for selecting one of the specific examinations;
upon input of the selection of the examination, the automatic scan planning module configures the MRI system automatically with the image acquisition settings corresponding to the selected specific examination;
wherein the MRI system comprises an image processing unit configured to receive the image data of a scout image which is acquired before setting the examination specific settings of the MRI system or of a reference image, the said image processing unit executing image processing of the scout image or of the reference image for determining the kind, the position and orientation of an image of one or more tissues, organs or anatomical details and automatically configuring lists of available alternative specific examinations and providing a selection organ for the user, for selecting one of the specific examinations which are filtered from a global list.

2. The MRI system according to claim 1, in which the automatic scan planning module comprises a database of anatomical districts corresponding to anatomical districts which are able to be subjected to MRI diagnostic examination, the said anatomical districts are related each one to one or more image acquisition settings and/or imaging protocols specifically suitable for a certain diagnosis.

3. The MRI system according to claim 1, in which the image acquisition settings comprise geometric parameters which are related to orientation and positioning of one or more image slices specifically suitable for imaging a certain anatomical district and for a certain diagnosis and physical parameters which relates to imaging settings like a specific sequence and other parameters.

4. The MRI system according to claim 1, wherein the display being configured to display a selection list of anatomic districts, each anatomic district being selectable by the input organs and providing a link to a list of specific diagnoses related to the selected anatomic district, the selection of a diagnosis being automatically related to the specific image acquisition settings and triggering an automatic application of the said image acquisition settings to the MRI apparatus.

5. The MRI system according to claim 1, wherein the display is further configured to enable a user to modify at least one of the factory pre-defined and empirically determined combinations of settings of the MRI system corresponding to a selection of a specific anatomical district and/or kind of examination.

6. The MRI system according claim 1, wherein the hardware processor is further configured to automatically identify the kind, the position and orientation in the scout image or in the reference image of one or more tissues, organs or anatomical details and to automatically select and apply the image acquisition settings suitable for the said automatically identified kind, position and orientation in the scout image of one or more tissues, organs or anatomical details.

7. The MRI system according to claim 5, wherein the said factory pre-defined, experimentally and empirically determined settings are at least one or a combination of at least two of the following parameters: region of interest (ROI), orientation of image slices, number of image slices and position in relation to the ROI, resolution, excitation sequence, slice thickness.

8. An MRI system comprising:
a cavity for accommodating a target body under examination or a part thereof;
a magnet for generating a static magnetic field in a volume of space;
gradient coils for generating gradient magnetic fields in addition to the static magnetic field according to three spatial directions;
a hardware processor configured to drive and control the gradient coils and the magnet;
a transmission antenna connected to an excitation signal sequence generator for transmitting spin echo excitations signals into the cavity housing the target body;

a receipt antenna for receiving the MRI signals caused by
the excitation signals;
the hardware processor further configured to process the
MRI signals and extracting image data information and
for generating images;
a display for displaying the generated images;
the hardware processor further configured to manage the
excitation signal sequence generator and the display;
the display configured to enable a user to input MRI
image acquisition settings to be specified by the user
before starting with an image acquisition session;
an automatic scan planning module comprising a memory
in which a look up table or a database of examination
specific settings of the MRI system is stored respectively associating a specific kind of examination with a
factory pre-defined and empirically determined combination of settings of the MRI system, the said automatic
scan planning module controlling the display to display
a list of alternative specific examinations and providing
a selection organ for the user, for selecting one of the
specific examinations;
upon input of the selection of the examination, the automatic scan planning module configures the MRI system
automatically with the image acquisition settings corresponding to the selected specific examination;
wherein the hardware processor includes or is connected
to a memory configured to store a database of scout
images or a database of reference images and corresponding imaging slice orientations for each anatomic
district and each specific diagnosis, the hardware processor being configured to process the scout images
acquired for an imaging session for automatically identifying the anatomic district and applying a position and
orientation of the slice along which an image is to be
acquired according to an imaging protocol which is
specific for a certain diagnosis and is stored in the said
database.

9. A method for controlling image appearance features in
an MRI system, which method comprises:
providing a look up table or a database of examination
specific settings of an MRI system respectively associating a specific kind of examination with a factory
pre-defined and empirically determined combination of
settings of the MRI system,
providing a display configured to display a list of specific
examinations which are selectable by the user through
the display;
automatically configuring the MRI system with the factory pre-defined and empirically determined combination of settings of the MRI system corresponding to the
selected specific examination in the said look up table
or in the said database;
carrying out the MRI examination with the above defined
configuration of the MRI-system;
wherein the method further comprises:
acquiring a scout image before setting the examination
specific settings of the MRI system;
the scout image being processed by an imaging processing tool for determining the kind, the position and
orientation in the image of one or more tissues, organs
or anatomical details, and
automatically configuring lists of available alternative
specific examinations, and
providing a selection organ for the user, for selecting one
of the specific examinations which are filtered from a
global list using as a filter the output of the image
processing tool.

10. The method according to claim 9, further comprising:
providing a list of anatomic districts which are able to be
subjected to MRI examination for a respective diagnosis of one or more pathologies;
linking each anatomic district to the respective diagnosis;
linking each of the respective diagnosis to one or more
specific examinations;
displaying the list of the anatomic districts;
automatically displaying a list of diagnoses related to an
anatomic district upon selection of the said anatomic
district;
automatically selecting the factory pre-defined and
empirically determined combination of settings of the
MRI system corresponding to the selected specific
examination and
automatically configuring the MRI system according to
the said settings of the MRI system.

11. The method according to claim 9, wherein when for a
diagnosis there are available in the database two or more
different factory pre-defined and empirically determined
combinations of settings of the MRI system, the method
provides for displaying the two or more different factory
pre-defined and empirically determined combinations of
settings of the MRI system for selection by the user and
applying the factory pre-defined and empirically determined
combination of settings of the MRI system which has been
selected by the user.

12. The method according to claim 9, wherein the predefined settings can be modified by the user after having
selected a specific diagnosis and the said modified settings
may be stored as an alternative user pre-defined setting and
is suggested together or in place of the originally factory
pre-defined settings.

13. The method according to claim 9, wherein the predefined settings are at least one or a combination of at least
two of the following parameters: region of interest (ROI),
orientation of image slices, number of image slices and
position in relation to the ROI, resolution, excitation
sequence, slice thickness.

14. The method according to claim 9, wherein the method
is directed to an automatic positioning and orientation of
image slices for a specific anatomic district and a specific
diagnosis of a pathology of the said anatomic district, and
which method provides the following steps:
selecting an anatomic district corresponding to an object
to be examined;
selecting an imaging parameters setting among preconfigured available imaging settings for the said anatomic
district suitable for a diagnosis of a pathology of the
said anatomic district;
the said imaging settings comprising position and orientation information of the image slices to be acquired in
relation to the diagnosis of the pathology of the anatomic district and in relation scout images of a scout
image database of the said anatomic district;
the scout image comprises at least images along three
slices, each slice being oriented along one orthonormal
planes oriented along the transversal, coronal and sagittal direction;
processing the acquired scout image for identifying anatomic references common to the scout images of a
scout image database of the same anatomic district of
the acquired scout images of the anatomic district under
examination;
shifting the acquired scout image relatively to the scout
images of a scout image database in order to register the
anatomic references on the acquired scout image of the object under examination with the corresponding anatomic references on the scout images of the scout image database of the same anatomic district, and applying the position and orientation of the image slices related to the scout images in the scout image database to the acquired scout image of the object in examination.

15. The method according to claim 9, wherein the settings for acquiring images comprise also physical parameter settings of the MRI imaging process.

16. The method according to claim 9, wherein the imaging processing tool is an object recognition tool.

17. An MRI system comprising:
a cavity for accommodating a target body under examination or a part thereof;
a magnet for generating a static magnetic field in a volume of space;
gradient coils for generating gradient magnetic fields in addition to the static magnetic field according to three spatial directions;
a hardware processor configured to drive and control the gradient coils and the magnet;
a transmission antenna connected to an excitation signal sequence generator for transmitting spin echo excitations signals into the cavity housing the target body;
a receipt antenna for receiving the MRI signals caused by the excitation signals;
the hardware processor further configured to process the MRI signals and extracting image data information and for generating images;
a display for displaying the generated images;
the hardware processor further configured to manage the excitation signal sequence generator and the display;
the display configured to enable a user to input MRI image acquisition settings to be specified by the user before starting with an image acquisition session;
an automatic scan planning module comprising a memory in which a look up table or a database of examination specific settings of the MRI system is stored respectively associating a specific kind of examination with a factory pre-defined and empirically determined combination of settings of the MRI system, the said automatic scan planning module controlling the display to display a list of alternative specific examinations and providing a selection organ for the user, for selecting one of the specific examinations;
upon input of the selection of the examination, the automatic scan planning module configures the MRI system automatically with the image acquisition settings corresponding to the selected specific examination;
wherein the hardware processor is further configured to:
receive the image data of a scout image which is acquired before setting the examination specific settings of the MRI system or of a reference image,
determine the kind, position and orientation in the scout image of one or more tissues, organs or anatomical details, and
automatically configure the list of alternative specific examinations.

18. The MRI system according claim 17, wherein hardware processor is also configured to provide a selection organ for the user.

* * * * *